United States Patent
Blackburn et al.

(10) Patent No.: US 9,045,431 B2
(45) Date of Patent: Jun. 2, 2015

(54) PROCESSES FOR THE PREPARATION OF 5-HT$_{2C}$ RECEPTOR AGONISTS

(75) Inventors: Anthony C. Blackburn, San Diego, CA (US); Anna Shifrina, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 133 days.

(21) Appl. No.: 13/701,471

(22) PCT Filed: Jun. 1, 2011

(86) PCT No.: PCT/US2011/038711
§ 371 (c)(1), (2), (4) Date: Nov. 30, 2012

(87) PCT Pub. No.: WO2011/153206
PCT Pub. Date: Dec. 8, 2011

(65) Prior Publication Data
US 2013/0158013 A1 Jun. 20, 2013

Related U.S. Application Data

(60) Provisional application No. 61/396,752, filed on Jun. 2, 2010.

(51) Int. Cl.
A61K 31/55 (2006.01)
C07D 223/16 (2006.01)
A61K 31/137 (2006.01)

(52) U.S. Cl.
CPC .............. *C07D 223/16* (2013.01); *A61K 31/55* (2013.01); *A61K 31/137* (2013.01)

(58) Field of Classification Search
CPC ............................. A61K 31/55; C07D 223/16
USPC ..................................... 514/212.07; 540/594
See application file for complete search history.

(56) References Cited

U.S. PATENT DOCUMENTS

| | | |
|---|---|---|
| 2,900,415 A | 8/1959 | Biel et al. |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,397,793 A | 3/1995 | Shaber et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,543 A | 9/1999 | Teng |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,466 B2 | 1/2007 | McClure et al. |
| 7,173,037 B2 | 2/2007 | Alonso-Alija et al. |
| 7,211,591 B2 | 5/2007 | Tajima et al. |
| 7,229,991 B2 | 6/2007 | Merla et al. |
| 7,230,024 B2 | 6/2007 | Carpino et al. |
| 7,232,823 B2 | 6/2007 | Carpino et al. |
| 7,514,422 B2 | 4/2009 | Smith et al. |

(Continued)

FOREIGN PATENT DOCUMENTS

| | | |
|---|---|---|
| AU | 515236 B2 | 3/1981 |
| CA | 1090797 | 12/1980 |

(Continued)

OTHER PUBLICATIONS

CAS Registry No. 006640-24-01 (2007).
CAS Registry No. 149454-12-6 (1993).
CAS Registry No. 620948-34-7 and 620948-93-8 (2007).
U.S. Appl. No. 60/372,058, filed Apr. 12, 2002, Arena Pharmaceuticals.
U.S. Appl. No. 60/405,495, filed Aug. 23, 2002, Arena Pharmaceuticals.
U.S. Appl. No. 60/434,607, filed Dec. 18, 2002, Arena Pharmaceuticals.
U.S. Appl. No. 60/479,280, filed Jun. 17, 2003, Arena Pharmaceuticals.
U.S. Appl. No. 60/512,967, filed Oct. 21, 2003, Arena Pharmaceuticals.
U.S. Appl. No. 60/638,221, filed Dec. 21, 2004, Arena Pharmaceuticals.
U.S. Appl. No. 60/789,191, filed Apr. 3, 2006, Arena Pharmaceuticals.

(Continued)

*Primary Examiner* — Brenda Coleman

(57) ABSTRACT

Processes and intermediates for preparing salts of the 5-HT$_{2C}$-receptor agonist (R)-8-chloro-1-methyl-2,3,4,5-tetrahydro-1H-3-benzazepine, and pharmaceutically acceptable solvates and hydrates thereof, that are useful for, inter alia, weight management.

28 Claims, 17 Drawing Sheets

(56) References Cited

U.S. PATENT DOCUMENTS

| | | |
|---|---|---|
| 7,704,993 B2 | 4/2010 | Smith et al. |
| 7,977,329 B2 | 7/2011 | Smith et al. |
| 8,153,621 B2 | 4/2012 | Behan et al. |
| 8,168,624 B2 | 5/2012 | Agarwal et al. |
| 8,168,782 B2 | 5/2012 | Weigl et al. |
| 8,207,158 B2 | 6/2012 | Smith et al. |
| 8,273,734 B1 | 9/2012 | Smith et al. |
| 8,299,241 B2 | 10/2012 | Gharbaoui et al. |
| 2003/0105106 A1 | 6/2003 | Chiang et al. |
| 2003/0225057 A1 | 12/2003 | Smith et al. |
| 2004/0101575 A1 | 5/2004 | Hinz |
| 2005/0020573 A1 | 1/2005 | Smith et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2009/0143576 A1 | 6/2009 | Weigl et al. |
| 2010/0004223 A1 | 1/2010 | Agarwal et al. |
| 2010/0173894 A1 | 7/2010 | Brian et al. |
| 2010/0305316 A1 | 12/2010 | Gharbaoui et al. |
| 2011/0015438 A1 | 1/2011 | Carlos et al. |
| 2012/0135982 A1 | 5/2012 | Smith et al. |
| 2012/0142967 A1 | 6/2012 | De Mattei et al. |
| 2012/0252786 A1 | 10/2012 | Behan et al. |
| 2012/0252787 A1 | 10/2012 | Anderson et al. |
| 2012/0252788 A1 | 10/2012 | Smith et al. |
| 2012/0264743 A1 | 10/2012 | Agarwal et al. |

FOREIGN PATENT DOCUMENTS

| | | |
|---|---|---|
| CA | 2197789 | 2/1996 |
| CA | 2325741 A1 | 10/1999 |
| CH | 500194 | 1/1971 |
| CN | 102126988 | 7/2011 |
| DE | 1944121 | 3/1970 |
| DE | 1914456 | 6/1971 |
| DE | 3315106 A1 | 11/1983 |
| DE | 3418270 | 11/1985 |
| EP | 0002765 A1 | 7/1979 |
| EP | 0007070 | 1/1980 |
| EP | 00027695 B1 | 10/1983 |
| EP | 0161350 A1 | 11/1985 |
| EP | 0174118 | 3/1986 |
| EP | 0080779 A1 | 7/1986 |
| EP | 0204349 | 12/1986 |
| EP | 245997 A2 | 11/1987 |
| EP | 0285287 A2 | 10/1988 |
| EP | 0285287 A3 | 10/1988 |
| EP | 0331130 A1 | 9/1989 |
| EP | 0331130 B1 | 9/1993 |
| EP | 0285919 B1 | 10/1994 |
| EP | 0096838 | 4/1997 |
| EP | 0987235 A1 | 3/2000 |
| EP | 1074549 A2 | 2/2001 |
| EP | 0987235 B1 | 3/2003 |
| EP | 1074549 B1 | 11/2003 |
| EP | 1411881 A2 | 4/2004 |
| EP | 1411881 B1 | 4/2005 |
| EP | 1838677 | 9/2009 |
| FR | 2518544 A1 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 62-267250 | 11/1987 |
| JP | 502723 | 8/1990 |
| JP | 5339263 | 12/1993 |
| JP | 6-62574 | 8/1994 |
| JP | 06298746 | 10/1994 |
| JP | 08134048 | 5/1996 |
| JP | 09030960 | 2/1997 |
| JP | 90987258 | 3/1997 |
| JP | 2000 44533 | 2/2000 |
| JP | 200176413 | 3/2001 |
| JP | 2001 89472 | 4/2001 |
| NL | 7807819 | 7/1978 |
| SU | 1238732 A3 | 6/1986 |
| WO | WO 88/07526 A1 | 10/1988 |
| WO | WO 88/07858 | 10/1988 |
| WO | WO 91/19698 | 12/1991 |
| WO | WO 93/00094 | 1/1993 |
| WO | WO 93/03015 | 2/1993 |
| WO | WO 93/16997 | 9/1993 |
| WO | WO 95/13274 | 5/1995 |
| WO | WO 96/04271 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02074746 | 9/2002 |
| WO | WO 03/000663 A1 | 1/2003 |
| WO | WO 03/027068 A2 | 4/2003 |
| WO | WO 03/057161 | 7/2003 |
| WO | WO 03/062205 | 7/2003 |
| WO | WO 03/062392 A2 | 7/2003 |
| WO | WO 03/086306 A2 | 10/2003 |
| WO | WO 03/086306 A3 | 2/2004 |
| WO | WO 2004/037788 | 5/2004 |
| WO | WO 2005/003096 A1 | 1/2005 |
| WO | WO 2005/019179 A2 | 3/2005 |
| WO | WO 2005/019179 A3 | 3/2005 |
| WO | WO 2005/019180 | 3/2005 |
| WO | WO 2005/042490 A1 | 5/2005 |
| WO | WO 2005/042491 A1 | 5/2005 |
| WO | WO 2005/082859 | 9/2005 |
| WO | WO 2006/006933 A2 | 1/2006 |
| WO | WO 2006/013209 A2 | 2/2006 |
| WO | WO 2006/043710 | 4/2006 |
| WO | WO 2006/069363 A2 | 6/2006 |
| WO | WO 2006/069363 A3 | 6/2006 |
| WO | WO 2006/071740 A2 | 7/2006 |
| WO | WO 2007/120517 A2 | 10/2007 |
| WO | WO 2007/120517 A3 | 10/2007 |
| WO | WO 2008/070111 A2 | 6/2008 |
| WO | WO 2008/070111 A3 | 6/2008 |
| WO | WO 2009/111004 | 9/2009 |
| WO | WO 2010/148207 | 12/2010 |

OTHER PUBLICATIONS

U.S. Appl. No. 60/873,036, filed Dec. 5, 2006, Arena Pharmaceuticals.
U.S. Appl. No. 61/068,102, filed Mar. 4, 2008, Arena Pharmaceuticals.
U.S. Appl. No. 61/268,930, filed Jun. 18, 2009, Arena Pharmaceuticals.
"Arena Pharmaceuticals Initiates Clinical Trial of Novel Anti-Obesity Drug", Press Release, Feb. 24, 2004, 1 page.
"Arena Pharmaceuticals Reports Successful Phase 1a Safety and Clinical Pharmacology Trial Results of Novel Anti-Obesity Compound", Press Release, Jul. 14, 2014, 2 pages.
"Arena Pharmaceuticals Initiates Phase 1b Clinical Trial of Novel Anti-Obesity Drug", Press Release, Jul. 26, 2004, 1 page.
"Arena Pharmaceuticals Announces Results of its Phase 1b Safety Study for its Novel Anti-Obesity Compound", Press Release, Nov. 3, 2004, 2 pages.
"Arena Pharmaceuticals Announces Results of its Phase 1b Safety Study for its Novel Anti-Obesity Compound", Press Release, Nov. 30, 2004, 2 pages.
"Arena Pharmaceuticals Initiates Phase 2 Efficacy Study for its Novel Anti-Obesity Compound", Press Release, Dec. 22, 2004, 2 pages.
Bagnol et al., "Obesity and Hypothalamic Signaling: Role of GPCRs", Presentation, Arena Pharmaceuticals, Inc., Jul. 30, 2010, 30 pages.

(56) References Cited

OTHER PUBLICATIONS

Baindur et al., "(±)-3-allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).
Barbière, "Estérification nitrique et nitration d'amino-alcools," Bulletin de la SociétéChimique de France, (1994), 5(11):470-480.
Barnes, "Pharmacological Strategies for Relapse Prevention in Schizophrenia," Psychiatry 3(10): 37-40 (2004).
Bickerdike, "5-HT$_{2C}$ Receptor Agonists as Potential Drugs for the Treatment of Obesity," Current Topics in Medicinal Chemistry, vol. 3:pp. 885-897 (2003).
Biel, Bronchodilators, N-substituted derivatives of 1-(3',4'-dihydroxyphenyl)-2-aminoethanol (arterenol) (1954) JACS 76:3149.
Binetti et al. Behavior disorders in Alzheimer disease: a transcultural pperspective. Arch Neurol. vol. 55, pp. 539-544 (1998).
Bosch et al., "Studies on the Synthesis of Pentacyclic Strychnos Indole Alkaloids. Photocyclization of N-chloroacetyl-1,2,3,4,5,6-hexahydro-1,5-methanoazocino [4,3-b] Indole Derivatives," Tetrahedron, 41(12):2557-66 (1985).
Bos et al., "Novel agonists of THT2C receptors. Synthesis & biological evaluation of substituted 2-{Indol-1-yl)-1-methylethylamines and 2-(Indeno[1,2-b]pyrrol-1-yl)-1-methylethylamines." Improved Therapeutics for Obsessive Compulsive Disorder, J. Med. Chem (1997), 40(17), 2762-2769.
Bremner "Seven Membered Rings", Institute for Biomolecular Science, Dept. of Chemistry, University of Wollongong; "Progress in Heterocyclic Chemistry 13," Pergamon Press, Ch. 7:340-77 (2001).
Callahan et al., "Fluoxetine Increases the Anorectic and Long-Term Dopamine-Depleting Effects of Phentermine", Synapse, Dec. 15, 2000; 38(4):471-6.
CAS Reg. No. 149454-12-6 ( Aug. 20, 1993).
CAS Reg. No. 27487-50-9 Nov. 16, 1984.
CAS Reg. No. 27487-51-0 Nov. 16, 1984.
CAS Reg. No. 400878-20-8 Mar. 14, 2002.
CAS Reg. No. 46906-45-0 Nov. 16, 1984.
Casy, et al., "Some Arylalkylamino Analogs of Acyclic Analgetics", J Med Chem., (1968), 11 (3):599-601.
Chahal et al., IDdb Meeting Report May 17-18, 2000.
Chang et al., "Dopamine Receptor Binding Properties of Some 2,3,4,5-tetrahydro-1H-3-benzazepine-7-OLS with Non-Aromatic Substituents in the 5-Position," Bioorganic & Medicinal Chemistry Letters, 2(5):399-402 (1992).
Chemical abstract (online) Accession No. 1980:407990, 1979.
Cheng, "Fen/Phen and Valvular Heart Disease: The Final Link Has Now Been Established", Circulation 2000;102;e180.
Chumpradit et al., "(±)-7-chloro-8-hydroxyl-1-(4'-[$^{125}$I]iodophenyl)-3-methyl-2,3,4,5-tetrahydro-1H-3-benzazepine: A Potential CNS D-1 Dopamine Receptor Imaging Agent," J. Med. Chem., 32:1431-35 (1989).
Clark et al., "1,9-alkano-bridged 2,3,4,5-tetrahydro-1H-3-benzazepines with Affinity for the α2-Adrenoceptor and the 5-HT$_{1A}$ Receptor," J. Med. Chem., 33:633-41 (1990).
Clinical Trial NCT00768612. "Study evaluating safety and tolerability of Fabicaserin in patients with sudden worsening of schizophrenia study." 2008.
Connolly et al., "Selections from Current Literature: Pharmacological Treatment of Obesity", Family Practice, vol. 15, No. 1, Oxford University Press 1998.
Deady et al., "Synthesis of Some Tetrahydro-2- and 3-benzazepines, and of Hexahydro-3-benzazocine," JCS Perkin I, 782-3 (1973).
Demarinis et al., "Development of an Affinity Ligand for Purification of α2-Adrenoceptors from Human Platelet Membranes," J. Med. Chem., 27, 918-921 (1984).
Dhonnchadha et al., "Anxiolytic-like effects of T-HT2c ligands on three mouse models of anxiety." Behav. Brain Res. 140:203-214 (2003).

Diagnostic and Statistical Manual of Mental Disorders, 4th edition, Text Revision, Washington, DC, American Psychiatric Association, 2000.
Di Chiara et al., "Nucleus accumbens shell and core dopamine: differential role in behavior and addiction," Behavioural Brain Research, 137: 75-114 (2002).
Di Chiara et al., "Reward System and Addiction: What Dopamine Does and Doesn't Do," Current Opinion in Pharmacology 7:69-76 (2007).
Di Giovanni et al., "Serotonin/dopamine interaction—Focus on 5-HT$_{2C}$ receptor, a new target of psychotropic drugs," Indian Journal of Experimental Biology, vol. 40:pp. 1344-1352 (2002).
Di Matteo et al. et al., "Role of 5-HT$_{2C}$ Receptors in the Control of Central Dopamine Function," Trends in Pharmacological Sciences 22(5):229-232 (2001).
Dixit et al. "Agents Acting on Central Nervous System: Part XXIII-2-Substituted 1, 2, 3, 4, 6, 7, 12, 12a-Octahydropyrazino[2,1-b][3] benzazepines & 3-Substituted 1, 2, 3, 4, 4a, 5, 6, 11-Octahydropyrazino[I,2-b][2] benzazepines," CDRI Communication No. 1969, 893-97 (1974).
Draper et al., "Novel Stereoselective Syntheses of the Fused Benzazepine Dopamine D$_1$ Antagonist (6aS, 13bR)-11-chloro-6, 6a, 7,8,9, 13b-hexahydro-7-methyl-5H-benzo[d]naphth[2, 1-b]azepin-12-ol (Sch 39166): 1. Aziridinium Salt Based Syntheses," Organic Process Research & Development, 2(3):175-85 (1998).
Flannery-Schroeder, "Reducing Anxiety to Prevent Depression," Am. J. Prev. Med. 31 (6S1):S136-S142 (2006).
Frankel et al., "Brain serotonin transporterdistribution in subjects with impulsive aggressivity: a positron emission study with [11C]McN 5652." Am. J. Psychiatry vol. 162:915-923 (2005).
Fuchs et al., "Total synthesis of (+/−)-lennoxamine and (+/−)-aphanorphine by intramolecular electrophilic aromatic substitution reactions of 2-amidoacroleins," Organic Letters, 2001, pp. 3923-3925, 3(24).
Gallant et al., "U-22,394A: a controlled evaluation in chronic schizophrenic patients," Current Therapy Research 9(11):579-81(1967).
Gardent et al., "Sur Quelques Propriétés de l'Amino-2 Bromo-4 1H Benzazépine-3 et de ses dérivés," Bulletin de La Société Chimique de France, 2:600-5 (1968) French Lang Only.
Garrison, "Defining obsexity: an adventure in cardiovascular disease epidemiology." J. Nutritional Biochem. (1998), 9(9), 493-500.
Gerace et al., "Predictors of Weight Increases over 7 Years in Fire Fighters and Paramedics," Preventive Medicine 25:593-600 (1996).
Gerritz et al., "Two General Routes to 1,4-disubstituted-2,3,4,5-tetrahydro-1H-3-benzazepines," Organic Letters, 2(25):4099-102 (2000).
Gobert et al., "Serotonin$_{2C}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).
Gombar et al., "Pharmacokinetics of a series of 6-chloro-2, 3, 4, 5-tetrahydro-3-substituted-1H-3-benzazepines in rats," Drug Metab. Disposition 16:367-372 (1988).
Greene et al., Protective Groups in Organic Syntheses, 2nd Ed., Wiley and Sons, NY (1991).
Greisser "Polymorphism in the Pharmaceutical Industry," ed. Rolf Hilfier, Wiley-VCH Verlag GmbH & Co.: pp. 211-233 (2006).
Guillory, "Polymorphism in Pharmaceutical Solids," ed. Harry G. Brittain, Marcel Dekker, Inc., vol. 95: pp. 202-209 (1999).
Halford, "Serotonergic Drugs: Effects on Appetite Expression and Use for the Treatment of Obesity," Drugs 67(1):27-55 (2007).
Halford et al., "o-phenylenediacetimide and Other Compounds Related to 3,1H-benzazepine," J. Org. Chem. 17:1646-52 (1952).
Halford,, J.C.G., "Obesity Drugs in Clinical Development," Current Opinion in Investigational Drugs 7(4):312-318 (2006).
Hasan et al.,., "Syntheses of N-chloroacyl-β-phenylethylamine Derivatives," Indian J. Chem., 9:1022-4 (1971).
Hashima, "Syntheses and biological activities of the marine bryozoan alkaloids convolutamines A, C and F and Lutamides A and C." Bioorg & Med. Chem. 8:1757, 2000.
Hassine-Coniac, et al., et al., "Preparation et propriétés d'aldéhydes dans la série de la benzazépine-3," Bulletin de La Société Chimique de France, 11:3985-92 (1971) French Lang Only.

(56) References Cited

OTHER PUBLICATIONS

Haynes et al. "Occurrence of pharmaceutically acceptable anions and cations in the Cambridge Structural Database," J. Pharm. Sci. 94:10, pp. 2111-2120 (Oct. 2005).
Hazebroucq, "Accès A Des $_l$-H, Tètrahydro-2, 3, 4,5 Benzazèpines-$_3$ One-$_l$, et a Des Hexahydro Imidazo Isoquinoléines," Ann. Chim., t.I:221-54 (1966) French Lang Only.
Heisler et al., "Activation of Central Melanocortin Pathways by Fenfluramine", Science, vol. 297, Jul. 26, 2002.
Helferich et al,. "Uber Derivate Einger chinolincarbonsauren," J. Fur Praktische Chemie, vol. 33, 1966, 39-48.
Hester et al., "Azepinoindoles. I. Hexahycloroazepino[4,5-b]indoles," J. Med. Chem. 11(1): 101-106 (1968).
Heys et al., "A New Entry into C7-0xygenated Tetrahydro-1$H$-3-benzazepines: Efficient Labeling with Carbon-14 in the Benzo Ring," J. Org. Chem., 54(19):4702-6 (1989).
Higgins et al. "Serotonin and drug reward: focus on 5-HT$_{2C}$ receptors," European Journal of Pharmacology, 480: 151-162 (2003).
Hitzig, P., "Combined serotonin and dopamine indirect agonists correct alcohol craving and alcohol-associated neuroses," Journal of Substance Abuse Treatment, 11(5):489-90 (1994).
Ichii, "Friedel-crafts aralkylation. II. The AlCl3 Ch2NO2-catalyzed phenethylation of benzene and toluend with 2-arylethyl chlorides in a nitromethane solution," Bulletin of the Chemical Society of Japan, (1972), 45(9):2810-2813.
Im et al., "Positive Allosteric Modulator of the Human 5-HT$_{2C}$ Receptor," Molecular Pharmacology, 64: 78-84 (2003).
Isaac, "The 5-HT2C receptor as a potential therapeutic target for the design of antiobesity and antiepileptic drugs." Drugs of the Futre (2001), 26(4), 383-393.
Jandacek, R.J., "APD-356 (Arena)," *Current Opinion in Investigational Drugs* (6(10):1051-1056 (2005).
Jenck, et al., "Antiaversive effects of 5HT2C receptor agonists and fluoxetine in a model of panic-like anxiety in rats," European Neuropsychopharmacology 8: 161 (1998).
Jensen et al., "Potential Role of New Therapies in Modifying Cardiovascular Risk in Overweight Patients with Metabolic Risk Facts," *Obesity* 14 (Suppl. 3):143S-149S (2006).
Kaiser et al., "6-(phenylthio)-substituted 2,3,4,5-tetrahydro-1$H$-3-benzazepines, a Novel Class of Dopamine Receptor Antagonists and Neuroleptics," J. Med. Chem., 23(9):975-6 (1980).
Karasu et al., (2000) Practice Guideline for the Treatment of Patients with Major Depressive Disorder.
Klein, "Outcome success in obesity." Obesity Res. (2001), 9(suppl. 4):354S-358S.
Klohr et al., "An Intramolecular Photocyclization to Form the Azepino[3,4,5-cd]Indole System," Synthetic Communications 18(7):671-4 (1988).
Koplan et al., "Preventing Childhood Obesity: Health in the Balance, Executive summary," (2005).
Krull et al. Synthesis and structure/NMDA receptor affinity relationships of 1-substituted tetrahydro-3-benzazepines. Bioorganic & Medicinal Chem. 12(6), 1439-1451, 2004.
Kuenburg et al., "Development of a Pilot Scale Process for the Anti-Alzheimer Drug (--)-Galanthamine Using Large-Scale Phenolic Oxidative Coupling and Crystallisation-Induced Chiral Conversion," Organic Process Research & Development, 3(6):425-31 (1999).
Lacivita et al., "Selective Agents for Serotonin$_{2C}$ (5-HTC$_{2C}$) Receptor," Current Topics in Medicinal Chemistry, vol. 6:pp. 1927-1970 (2006).
Ladd et al., "Synthesis of a Dopaminergic Binding of 2-Aryldopamine Analogues: Phenethylamines, 3-Benzazepines, and 9-(Aminomethyl) Fluorenes," B209 J. Med. Chem., 29(10):1904-12 (1986).
Lam et al., Canadian Consensus Guidelines for the Treatment of Seasonal Affective Disorder, Clinical & Academic Publishing, Vancouver, BC, Canada, 1999.
Lennon et al, "Azabenzocycloheptenones. Part XVIII.[1] Amines and Amino-ketones of the Tetrahydro-3-benzazepin-1-one Series," J.C.S. Perkin 1,7:622-6 (1975).
Lin et al, "Benzindene Prostaglandins. Synthesis of Optically Pure 15-Deoxy-U-68,215 and its Enantiomer via a Modified Intramolecular Wadsworth-Emmons-Wittig Reaction," J. Org. Chem., 52(25):5594-601 (1987).
Loke et al., "Appetite Suppressants and Valvular Heart Disease—A Systematic Review", BMC Clinical Pharmacology, 2002, 2:6, 10 pages.
MacDonald et al., "Design and Synthesis of *trans*-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1$H$-3-benzazepine (SB-414796): A Potent and Selective Dopamine D$_3$ Receptor Antagonist," J. Med. Chem., 46(23):4952-64 (2003).
Martin et al."5HT2C receptor agonists pharmacological characteristics and therapeutic potential." J. Pharmacol. Exp. Therap. (1998), 286(2), 913-924.
Millan et al., "5HT2C receptors mediate penile erections in rats: actions of novel and selective agonists and antagonists." Eur. J. Pharmacol. 325:9-12 (1997).
Modeshka (1990) Arch. Pharm. 323:829.
Moline et al., "Postpartum Depression: A Guide for Patients and Families," Expert Consensus Guidelines Series—Treatment of Depression in Woman 2001, Mar. 112-113 (2001).
Muller et al., "Intracellular 5-HT$_{2C}$-receptor dephosphorylation: a new target for treating drug addiction," Trends in Pharmacological Sciences, 27(9):455-58 (2006).
Nagase et al., "An anhydrous polymorphic form of trehalose," *Carbohydrate Research* 337(2),167-173 (2002).
Nagle et al., "Efficient Synthesis of β-amino Bromides," Tetrahedron Letters, 41:3011-4 (2000).
Nair et al., "Preparation of 2,3,4,5-tetrahydro-3,1H-benzazepine-2-one," Indian J. Chem., 5:169-70 (1967).
National Institute on Drug Abuse, Proc. 41st Ann. Scientific Mtg (1979), pp. 356-401.
Navarro-Vazquez et al., "A study of aryl radical cyclization in enaminone esters," J. Org. Chem. 67:3213-20 (2002).
Neumeyer et al., "Development of a High Affinity and Stereoselective Photoaffinity Label for the D-1 Dopamine Receptor: Synthesis and Resolution of 7-[$^{125}$I]Iodo-8-hydroxy-3-methyl-1-(4'-azidophenyl)-2,3,4,5-tetrahydro-1$H$-3-benzazepine," J. Med. Chem., 33(2):521-6 (1990).
Niendam et al., "Neurocognitive Performance and Functional Disability in the Psychosis Prodrome," Schizophrenia Research 84:100-111 (2006).
Ohnmacht et al., "Naphtho[2,1-b][1,5]-and [1,2-f][1,4]oxazocines as selective NK1 antagonists." Biorganic & Medicinal Chem. 2004, vol. 12, No. 10, pp. 2653-2666 (2004) Bioorg & Medicinal Chemistry 12:2653.
Okuno et al., "Photocyclization of N-chloroacetyl-2,5-dimethoxyphenethylamine. Synthesis of Pyrroloindoles," Chem. Pharm. Bull., 23(11):2584-90 (1975).
Orito et al., "Benzolactams-I: Alkylation of 1,2,4,5-tetrahydro-3-methyl-3H-3-benzazepin-2-one with sodium hydride and alkyl halide," Tetrahedron 36:1017-1021 (1980) Pergamon Press Ltd.
Orito et al., "Total synthesis of pseudo type of protopine alkaloids," Heterocycles 14(1), 11-14 (1980).
Orito, et al., "Synthetic Studies of heterocyclic compounds I. Alkylation and acylation of 1,2,4,5-tetrahydro-3-methyl-3H-3-benzazepin-2-one," CASREACT, 1979, 93:7990.
Paulekuhn et al., "Trends in active pharmaceutical ingredient salt selection based on analysis of the Orange Book Database." J. Med. Chem. 50:26, pp. 6665,6672 (2007).
Pauvert et al., "Silver Nitrate-Promoted Ring Enlargement of 1-tribromomethyl-1,2-dihydro- and 1-tribromethyl-1,2, 3,4-tetrahydro-isoquinoline Derivatives: Application to the Synthesis of the Anti-anginal Zatebradine," Tetrahedron Letters, 44:4203-6(2003), Pergamon Press Ltd.
Pawan et al., "Preliminary study on the effects of fenfluramine derivative, 'S992' in man," British Journal of Pharmacology, 41(2): 416P-417P (1971).
Pecherer et al., "The Synthesis of Some 7- and 7,8-substituted 2,3,4,5-tetrahydro-1H-3-benzazepines," J. Heterocyclic Chemistry 8(5):779-783 (1971).

(56) References Cited

OTHER PUBLICATIONS

Pecherer et al., "A Novel Synthesis of Aromatic Methoxy and Methylenedioxy Substituted 2,3,4,5-tetrahydro-1H-3-benzazepines," J. Het. Chem., 9:609-16 (1972).

Perry et al., "Prospective study of risk factors for development on non-insulin dependent diabetes in middle aged British men," BMJ (1995) 310:560-564.

Pfeiffer et al., "Dopaminergic Activity of Substituted 6-chloro-1-phenyl-2,3,4,5-tetrahydro-1H-3-benzazepines," J. Med. Chem., 25(4):352-8 (1982).

Piesla et al., (2001) Schizophrenia Research 49: 95.

Porras, et al., "5-HT2A and 5-HT2C/2B Receptor Subtypes Modulate Dopamine Release Induced in Vivo by Amphetamine and Morphine in Both the Rat Nucleus Accumbens and Striatum," Neuropsychopharmacology 26: 311-324 (2002).

Prous Science Integrity entry 156186, 2006.

Prous Science Integrity entry 354056, 2007.

Remington's Pharmaceutical Sciences 17th ed., Mack Publishing Company, Easton Pa.: 1418 (1985).

Rosenzweig-Lipson et al., "Vabicaserin: effects of a novel 5HT2C agaonist on medial prefrontal cortex neurotransmission, cognition and sensorimotor gating." 29th ECNP Congress, Vienna, Austria (2007).

Roth et al., "Anorectic Efficacy of the Fenfluramine/Phentermine Combination in Rats: Additivity or Synergy?", Eur J Pharmacol, Jun. 4, 1999, 373(2-3):127-34.

Rothman, R.B., "Treatment of Alcohol and Cocaine Addiction by the Combination of Pemoline and Fenfluramine: A Preliminary Case Series," Journal of Substance Abuse Treatment, 12(6):449-53 (1995).

Rothman et al., "Evidence of Possible Involvement of 5-HT$_{2B}$ Receptors in the Cardiac Valvulopathy Associated with Fenfluramine and Other Serotonergic Medications", American Heart Assocation, Inc., 2000, 2836-41.

Rowland et al., "Acute Anorectic Effect of Single and Combined Drugs in Mice Using a Non-deprivation Protocol", Psychopharmacology (Berl). Sep. 2001; 157(2):193-6.

Rowland et al., "Anorectic Effect of Dehydroepiandrosterone Combined with Dexfenfluramine or Thionisoxetine", Eur J Pharmacol, May 4, 2001; 419(1):61-4.

Rowland et al., "Effects of the Cannabinoid Receptor Antagonist SR 141716, Alone and In Combination with Dexfenfluramine or Naloxone, on Food Intake in Rats", Psychopharmacology (Berl)., Dec. 2001; 159(1):111-6. Epub Oct. 2, 2001.

Rowland et al., "Comparison of Either Norepinephrine-uptake Inhibitors or Phentermine Combined with Serotonergic Agents on Food Intake in Rats", Psychopharmacology (Berl)., Mar. 2000; 149(1):77-83.

Schaffner et al., "Preventing Severe Mental Illnesses—New Prospects and Ethical Challenges," *Schizophrenia Research* 51:3-15 (2001).

Schlademan et al., "Synthesis of oxo- and 1-hydroxy-azobenzocycloalkanes," J. Chem. Soc. Perkin Transacts. (1972) 2:213-215.

"Silver Lining to the Cloud Over Anorexogen-Related Cardiac Valvulpathy?", Editorial, Annals of Internal Medicine, vol. 134, No. 4, Feb. 20, 2001, 3 pages.

Silverstone, "Appetite Suppressants: a review." Drugs. 43:6, pp. 820,636 (Jun. 1992). Abstract.

Smith, "5-HT2C Receptor Agonists for the Treatment of Obesity", Presentation, Arena Pharmaceuticals, Inc., Jul. 28, 2010, 30 pages.

Smith, "Discovery of Lorcaserin (APD356): A Selective 5HT2C Agonist for the Treatment of Obesity", Presentation, Arena Pharmaceuticals, Inc., Jul. 21, 2006.

Smith et al., "Discovery and SAR of new benzazepines as potent and selective 5HT2C receptor agonists for the treatment of obesity." Bior. Med. Chem Leet. 15(5):1467-1470 (2005).

Smith et al, "Discovery and Structure-Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," J. Med. Chem. 2008, 51, 305-313.

Sussman et al., "Effects of Nefazodone on Body Weight: A Pooled Analysis of Selective Serotonin Reuptake Inhibitor- and Imipramine-Controlled Trails", J Clin Psychiatry 62:4, Apr. 2001; 256-60.

Tecott et al., "Eating disorder and epilepsy in mice lacking 5-HT2C serotonin receptors." Nature, 374:542-546 (1996).

Tietze et al., "Efficient synthesis of 2, 3, 4, 5-tetrahydro-1H-3-benzazepines by intramolecular Heck reaction," Papers, Synthesis 876:880 (Sep. 1993).

Tohda et al. "Molecular pathopharmacology of 5-HT2C receptors and the RNA editing in the brain." J. Pharma. Science vol. 100: 427-432 (2006).

Tsuang et al., "Towards the Prevention of Schizophrenia," B245 Biol. Psychiatry 48:349-356 (2000).

Van Oekelen et al., "5-HT$_{2A}$ and 5-HT$_{2C}$ receptors and their atypical regulation properties," Life Sciences, vol. 72:pp. 2429-2449 (2003).

Vanderlaan et al., "Synthesis and Oxidative Coupling of (±)-3-oxoreticuline," J. Org. Chem., 50(6):743-7 (1985).

Vink et al., "Risk Factors for Anxiety and Depression in the Elderly: A Review," J. Affect. Disord., vol. 106, p. 29-44 (2008).

Webb, "APD356, A Potential New Treatment for Obesity", Presentation, Arena Pharmaceuticals, Inc., Aug. 11, 2005, 43 pages.

Weinstock et al., "Separation of Potent Central and Renal Dopamine Agonist Activity in Substituted 6-chloro-2,3,4,5-tetrahydro-7,8-dihydroxy-1-phenyl-1H-3-benzazepines," J. Med. Chem., 23(9):973-5 (1980).

Wellman et al., "Synergistic Interactions Between Fenfluramine and Phentermine", Int J Obes Relat Metab Discord., Jul. 1999; 23(7):723-32.

Wilk, "Exchange type reactions between oxiranes or thiiranes and 2-hydroxyalkyl or 2-thioalkyl amines and sulfides." (1988) Pol. J. Chem. 62:895.

Williams, Chemistry Demystified 123 (2003).

Winkler, "Obesity and hemostasis." Archives of Gynecology & Obst. (1997), 261(1), 25-29.

Wise, "Addiction Becomes a Brain Disease," Neuron, 26: 27-33 (2000).

Wisner et al., "Postpartum Depression," N. Engl. J. Med., 347(3):194-199 (2002).

Woods et al., "Annual Report: Evaluation of New Compounds for Opoid Activity," National Institute on Drug Abuse, Proceedings of the 41st Annual Scientific Meeting (1979) pp. 356-401.

Wu et al., "Amino Diol Based Asymmetric Syntheses of a Fused Benzazepine as a Selective D1 Dopamine Receptor," Organic Process Research & Development, 1(5):359-64 (1997).

Yasuda et al., "A Novel and Stereoselective Synthesis of (±)-cephalotaxine and its Analogue," Tetrahedron Letters, 27(18):2023-6 (1986).

Yonemitsu et al., "Photolysis of N-Chloracetyle-O-methyl-L-tyrosine to an Azaazulene," Journal of the American Chemical Society, 89(4): 1039-40 (1967).

Yonemitsu, et al., "Photocyclization of Pharmacodynamic Amines. IV. Novel Heterocycles from N-chloroacetyl-3,4-dimethoxyphenethylamine," Journal of the American Chemical Society, 92(19):5686-90 (1970).

Yonemitsu et al., "Photocyclization of Pharmodynamic Amines. II. X-Ray Analysis of a Noncentrosymmetric Tetracyclic Indole," Journal of the American Chemical Society, 90(23):6522-3 (1968).

Yonemitsu et al., "Photocyclizations of Tyrosines, Tyramines, Catecholamines, and Normescaline," Journal of the American Chemical Society, 90(3):776-84 (1968).

Yoshinaga et al., "Prevention of Mildly Overweight Children from Development of More Overweight Condition," *Prevention Medicine* 38:172-174 (2004).

Zhang et al., (1994) Chem. Lett. 12:2271.

PROCESSES FOR THE PREPARATION OF 5-HT$_{2C}$ RECEPTOR AGONISTS

CROSS-REFERENCE TO RELATED APPLICATIONS

This is a 35 USC 371 National Stage Application of International Application No. PCT/US2011/038711, filed Jun. 1, 2011, which claims priority to U.S. Provisional Patent Application No. 61/396,752, filed Jun. 2, 2010, each of which is hereby incorporated by reference in its entirety.

FIELD

Provided are processes and intermediates for preparing salts of the 5-HT$_{2C}$-receptor agonist (R)-8-chloro-1-methyl-2,3,4,5-tetrahydro-1H-3-benzazepine, and pharmaceutically acceptable solvates and hydrates thereof, that are useful for, inter alia, weight management.

BACKGROUND

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. BMI is more highly correlated with body fat than any other indicator of height and weight. Overweight is defined as a BMI in the range 25-30 kg/m$^2$, and obesity as a BMI greater than 30 kg/m$^2$ (see table below).

| Classification Of Weight By Body Mass Index (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, *Semin Vasc Med*, 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: Orlistat (Xenical™) a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the 5-HT$_{2C}$ receptor plays an important role in the control of eating and in the anti-obesity effect of d-fenfluramine As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-$HT_{2C}$ receptor agonist can be a more effective and safe anti-obesity agent. Also, 5-$HT_{2C}$ knockout mice are overweight with cognitive impairment and susceptibility to seizure.

It is believed that the 5-$HT_{2C}$ receptor may play a role in obsessive compulsive disorder, some forms of depression, and epilepsy. Accordingly, agonists can have anti-panic properties, and properties useful for the treatment of sexual dysfunction.

In sum, the 5-$HT_{2C}$ receptor is a receptor target for the treatment of obesity and psychiatric disorders, and it can be seen that there is a need for selective 5-$HT_{2C}$ agonists which safely decrease food intake and body weight.

The salts of the present invention comprise the selective 5-$HT_{2C}$-receptor agonist (R)-8-chloro-1-methyl-2,3,4,5-tetrahydro-1H-3-benzazepine (Compound 1), which is useful for, inter alia, weight management, including weight loss and the maintenance of weight loss. Compound 1 is disclosed in PCT patent publication WO2003/086303, which is incorporated herein by reference in its entirety.

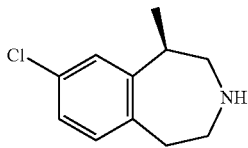

Various synthetic routes to (R)-8-chloro-1-methyl-2,3,4,5-tetrahydro-1H-3-benzazepine, its related salts, enantiomers, crystalline forms, and intermediates, have been reported in WO 2005/019179, WO 2006/069363, WO 2007/120517, WO 2008/070111, WO 2009/111004, and WO 2010/148207 each of which is incorporated herein by reference in its entirety.

Combinations of (R)-8-Chloro-1-methyl-2,3,4,5-tetrahydro-1H-3-benzazepine with other agents, including without limitation, phentermine, and uses of such combinations in therapy are described in WO 2006/071740, which is incorporated herein by reference in its entirety.

Various salts, crystalline forms, formulations, and uses of (R)-8-chloro-1-methyl-2,3,4,5-tetrahydro-1H-3-benzazepine, have been reported in U.S. provisional applications 61/402,578, 61/403,143, 61,402,580, 61/402,628, 61/403, 149, 61,402,589, 61/402,611, 61/402,565, and 61/403,18, each of which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-$HT_{2C}$ receptor and shows effectiveness at reducing obesity in animal models and humans. In December 2009, Arena Pharmaceuticals, Inc. submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

In view of the growing demand for compounds useful in the treatment of disorders related to the 5-$HT_{2C}$ receptor, (R)-8-chloro-1-methyl-2,3,4,5-tetrahydro-1H-3-benzazepine has emerged as an important new compound. Accordingly, new processes and intermediates for the production of (R)-8-chloro-1-methyl-2,3,4,5-tetrahydro-1H-3-benzazepine salts are needed. The processes and intermediates described herein help meet these and other needs.

SUMMARY

A priori, it is difficult to predict crystal structures with confidence: even for crystals with relatively few atoms per unit cell, the number of possibilities is prohibitively large. In addition, a person of ordinary skill in the art cannot know beforehand exactly how many polymorphs of a given compound exist and under what conditions they will appear.

A failure in selection of the most suitable polymorphs may result in serious trouble in industrial processes and in the end use of products. For example it may lead to difficulties of solid-liquid separation. With particular reference to pharmaceuticals, polymorphism often needs to be controlled, as this may affect characteristics of medicines such as stability and bioavailability. Consequently, the control of polymorphs is a problem in industrial crystallization.

During the course of polymorph screening of Compound 1 hydrochloride, a new crystal phase has been discovered. This crystal form is an anhydrous polymorph designated Compound 1 hydrochloride salt Form IV. In 124 attempts, it did not crystallize from homogeneous supersaturated solution. It was discovered instead during screening for solution-mediated phase transformation (SMPT) of other Compound 1 hydrochloride salt forms under near anhydrous conditions. At ambient temperature, Compound 1 hydrochloride salt Form IV is the most stable of the three anhydrous polymorphs described herein, although it is not thermodynamically favored over the pseudo-polymorph Compound 1 hydrochloride salt hemihydrate Form III, at % RH≥20.

One aspect of the present invention pertains to certain processes for preparing (R)-8-chloro-1-methyl-2,3,4,5-tetrahydro-1H-3-benzazepine hydrochloride salt hemihydrate Form III, via (R)-8-chloro-1-methyl-2,3,4,5-tetrahydro-1H-3-benzazepine hydrochloride salt Form IV.

One aspect of the present invention pertains to a salt which is (R)-8-chloro-1-methyl-2,3,4,5-tetrahydro-1H-3-benzazepine hydrochloride salt Form IV.

DETAILED DESCRIPTION

Figure 1:
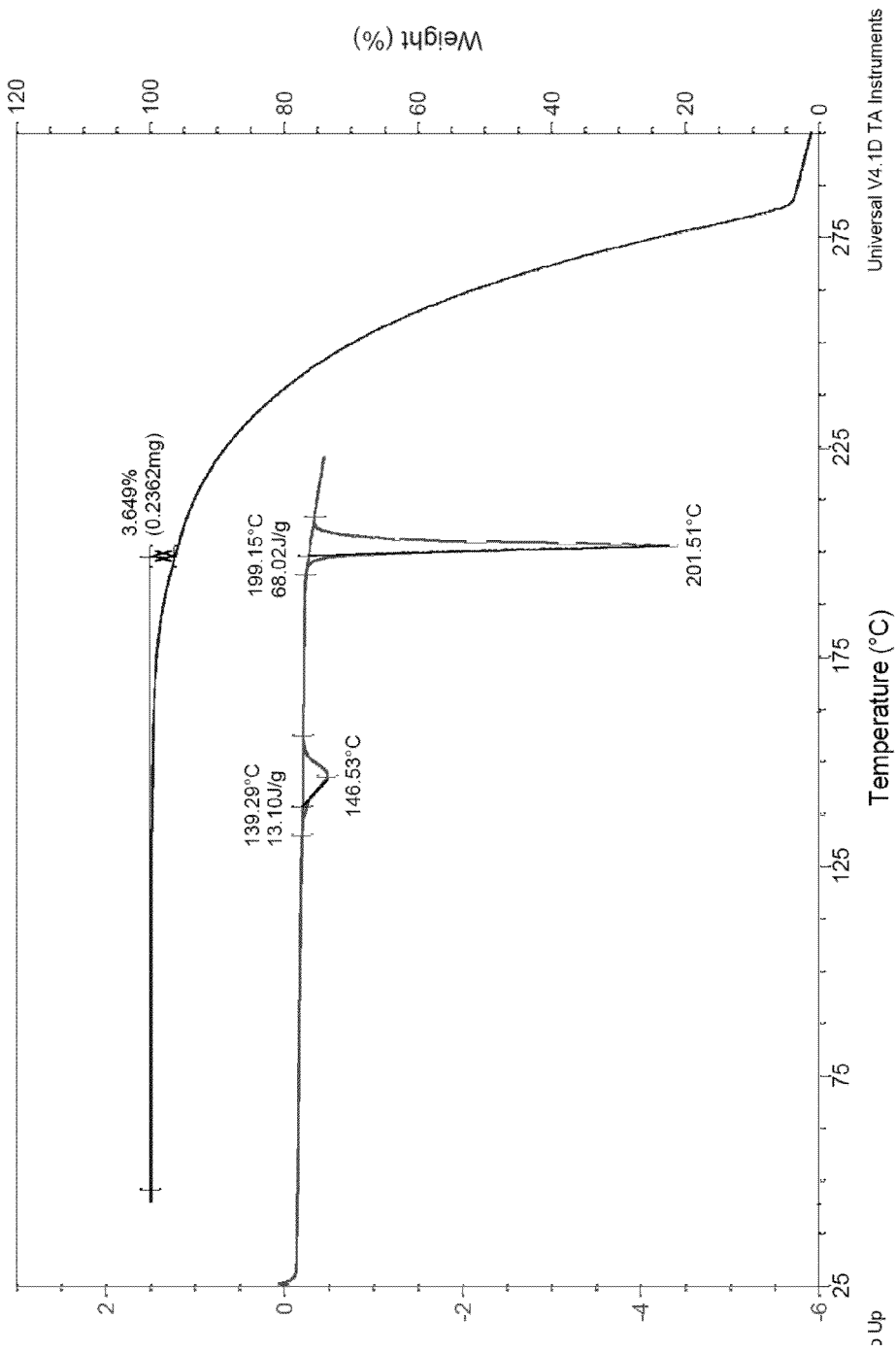
FIG. 1: DSC and TGA of Compound 1 Hydrochloride Salt Form I.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The present disclosure includes all isotopes of atoms occurring in the present compounds, salts, and crystalline forms. Isotopes include those atoms having the same atomic number but different mass numbers. By way of general example, and without limitation, isotopes of hydrogen include $^2H$ (deuterium) and $^3H$ (tritium). Isotopes of carbon include $^{13}C$ and $^{14}C$.

Definitions

For clarity and consistency, the following definitions will be used throughout this patent document.

The term "agonists" is intended to mean moieties that interact and activate a receptor, such as the 5-HT$_{2C}$ serotonin receptor, and initiate a physiological or pharmacological response characteristic of that receptor, for example, moieties that activate the intracellular response upon binding to the receptor, or enhance GTP binding to membranes.

The term "solution-mediated phase transformation (SMPT)" as used herein means the conversion of a crystal form or forms in a stirred slurry to a slurry of a more thermodynamically stable crystal form.

The term "water activity (a$_w$)" as used herein means the ratio of vapor pressure exerted by water in a substance to the vapor pressure of pure water, at the same temperature. Stated in equation form: $a_w = (P/Po)_T$ (where P equals the equilibrium vapor pressure of the water in the substance and Po is the vapor pressure of pure water, at the same temperature).

Processes

The present invention is directed, inter alia, to processes and intermediates useful in the preparation of (R)-8-chloro-1-methyl-2,3,4,5-tetrahydro-1H-3-benzazepine and pharmaceutically acceptable salts, solvates and hydrates there of (R)-8-chloro-1-methyl-2,3,4,5-tetrahydro-1H-3-benzazepine is a selective 5-HT$_{2C}$-receptor agonist that is useful in weight management and in the treatment of obesity, schizophrenia, anxiety, depression, psychoses and alcohol addiction.

The processes described herein can be monitored according to any suitable method known in the art. For example, product formation can be monitored by differential scanning calorimetry (DSC), X-ray powder diffraction (PXRD), and other solid state methods.

The processes described herein can be carried out in suitable solvents which can be readily selected by one of skill in the art of chemistry. Suitable solvents can be substantially nonreactive with the starting materials, the intermediates, or products at the temperatures at which the processes are carried out, e.g., temperatures which can range from the solvent's freezing temperature to the solvent's boiling temperature. A given process can be carried out in one solvent or a mixture of more than one solvent.

Suitable solvents can include halogenated solvents such as: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, 1,2-dichlorobenzene, 1,3-dichlorobenzene, 1,4-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane, and hexafluoroethane.

Suitable solvents can include ether solvents, such as dimethoxymethane, tetrahydrofuran, 2-methyltetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, and t-butyl methyl ether.

Suitable solvents can include protic solvents, such as: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable solvents can include aprotic solvents, such as: benzene, cyclohexane, pentane, hexane, toluene, cumene, cycloheptane, methylcyclohexane, heptane, ethylbenzene, o-, m-, or p-xylene, octane, indane, nonane, naphthalene, tetrahydrofuran, acetonitrile, dimethyl sulfoxide, propionitrile, ethyl formate, methyl acetate, hexachloroacetone, acetone, ethyl methyl ketone, ethyl acetate, isopropyl acetate, sulfolane, 1,3-dimethyl-3,4,5,6-tetrahydro-2(1H)-pyrimidinone, 1,3-dimethyl-2-imidazolidinone, N-methylpyrrolidinone, tetramethylurea, nitromethane, and nitrobenzene.

The processes described herein can be carried out at appropriate temperatures which can be readily determined by one skilled in the art. Process temperatures will depend on, for example, the melting and boiling points of the solvent, and the thermodynamics and kinetics of the process.

The processes described herein can be carried out in air or under an inert atmosphere.

Upon carrying out the processes described herein, the usual isolation and purification operations such as concentration, filtration, extraction, solid-phase extraction, recrystallization, chromatography, and the like may be used, to isolate the desired products.

Example processes and intermediates of the present invention are provided below in Scheme I.

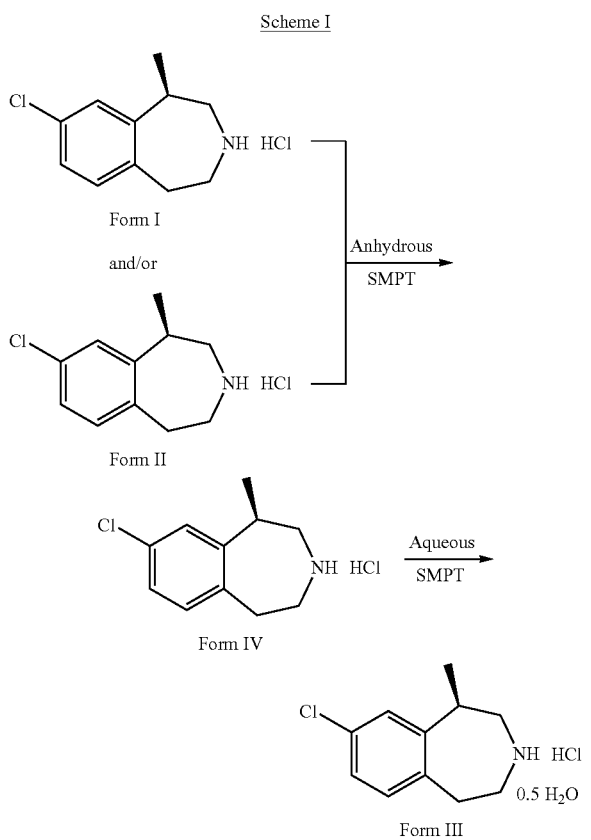

Scheme I

Form I
and/or

Form II

Anhydrous SMPT →

Form IV

Aqueous SMPT →

Form III

One aspect of the present invention pertains to processes, such as those exemplified by Scheme I (supra).

One aspect of the present invention pertains to processes for preparing (R)-8-chloro-1-methyl-2,3,4,5-tetrahydro-1H-3-benzazepine hydrochloride salt hemihydrate Form III, comprising slurrying a first mixture comprising: (R)-8-chloro-1-methyl-2,3,4,5-tetrahydro-1H-3-benzazepine hydrochloride salt Form IV; and a first solvent; to form the (R)-8-chloro-1-methyl-2,3,4,5-tetrahydro-1H-3-benzazepine hydrochloride salt hemihydrate Form III.

In some embodiments, the first mixture has a water activity of greater than about 0.10.

In some embodiments, the first mixture has a water activity of greater than about 0.11.

In some embodiments, the first mixture has a water activity of greater than about 0.12.

In some embodiments, the first mixture has a water activity of greater than about 0.13.

In some embodiments, the first mixture has a water activity of greater than about 0.14.

In some embodiments, the first mixture has a water activity of greater than about 0.15.

In some embodiments, the first mixture has a water activity of greater than about 0.16.

In some embodiments, the first mixture has a water activity of greater than about 0.17.

In some embodiments, the first mixture has a water activity of greater than about 0.18.

In some embodiments, the first mixture has a water activity of greater than about 0.19.

In some embodiments, the first mixture has a water activity of greater than about 0.20.

In some embodiments, the (R)-8-chloro-1-methyl-2,3,4,5-tetrahydro-1H-3-benzazepine hydrochloride salt Form IV is prepared by slurrying a second mixture comprising: a starting material selected from (R)-8-chloro-1-methyl-2,3,4,5-tetrahydro-1H-3-benzazepine hydrochloride salt Form I, (R)-8-chloro-1-methyl-2,3,4,5-tetrahydro-1H-3-benzazepine hydrochloride salt Form II, and mixtures thereof; and a second solvent; to form the (R)-8-chloro-1-methyl-2,3,4,5-tetrahydro-1H-3-benzazepine hydrochloride salt Form IV.

In some embodiments, the process further comprises isolating the (R)-8-chloro-1-methyl-2,3,4,5-tetrahydro-1H-3-benzazepine hydrochloride salt Form IV.

In some embodiments, the second mixture further comprises seed crystals, wherein the seed crystals comprise (R)-8-chloro-1-methyl-2,3,4,5-tetrahydro-1H-3-benzazepine hydrochloride salt Form IV.

In some embodiments, the starting material comprises (R)-8-chloro-1-methyl-2,3,4,5-tetrahydro-1H-3-benzazepine hydrochloride salt Form I.

In some embodiments, the starting material comprises (R)-8-chloro-1-methyl-2,3,4,5-tetrahydro-1H-3-benzazepine hydrochloride salt Form II.

In some embodiments, the second mixture has a water activity of less than about 0.20.

In some embodiments, the second mixture has a water activity of less than about 0.19.

In some embodiments, the second mixture has a water activity of less than about 0.18.

In some embodiments, the second mixture has a water activity of less than about 0.17.

In some embodiments, the second mixture has a water activity of less than about 0.16.

In some embodiments, the second mixture has a water activity of less than about 0.15.

In some embodiments, the second mixture has a water activity of less than about 0.14.

In some embodiments, the second mixture has a water activity of less than about 0.13.

In some embodiments, the second mixture has a water activity of less than about 0.12.

In some embodiments, the second mixture has a water activity of less than about 0.11.

In some embodiments, the second mixture has a water activity of less than about 0.10.

In some embodiments, the second mixture has a water activity of less than about 0.09.

In some embodiments, the second mixture has a water activity of less than about 0.08.

In some embodiments, the second mixture has a water activity of less than about 0.07.

In some embodiments, the second mixture has a water activity of less than about 0.06.

In some embodiments, the second mixture has a water activity of less than about 0.05.

In some embodiments, the second mixture has a water activity of less than about 0.04.

In some embodiments, the second mixture has a water activity of less than about 0.03.

In some embodiments, the second mixture has a water activity of less than about 0.02.

In some embodiments, the second mixture has a water activity of less than about 0.01.

In some embodiments, the second solvent comprises an anhydrous solvent selected from: acetonitrile, isobutanol, acetone, and isopropanol.

In some embodiments, the second solvent comprises anhydrous acetonitrile.

One aspect of the present invention pertains to crystalline salts produced by a process of the present invention.

One aspect of the present invention pertains to processes of the present invention, further comprising admixing the (R)-8-chloro-1-methyl-2,3,4,5-tetrahydro-1H-3-benzazepine hydrochloride salt hemihydrate Form III with a pharmaceutically acceptable carrier.

One aspect of the present invention pertains to compositions produced by a process of the present invention.

One aspect of the present invention pertains to processes of the present invention, further comprising formulating the (R)-8-chloro-1-methyl-2,3,4,5-tetrahydro-1H-3-benzazepine hydrochloride salt hemihydrate Form III into a pharmaceutical composition.

One aspect of the present invention pertains to pharmaceutical compositions produced by a process of the present invention.

One aspect of the present invention pertains to compositions comprising a salt of the present invention.

One aspect of the present invention pertains to pharmaceutical compositions comprising a salt of the present invention.

Crystalline Salts

Polymorphism is the ability of a substance to exist as two or more crystalline phases that have different arrangements and/or conformations of the molecules in the crystal lattice. Polymorphs show the same properties in the liquid or gaseous state but they often behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily and may be thermodynamically favored over anhydrous polymorphs.

By way of example, Stahly recently published the results of polymorph screens of 245 compounds, which revealed that about 90% of them exhibited multiple solid forms. Overall, approximately half the compounds were polymorphic, often having one to three polymorphs. About one-third of the compounds formed hydrates, and about one-third formed solvates. Data from cocrystal screens of 64 compounds showed that 60% formed cocrystals other than hydrates or solvates. (G. P. Stahly, Crystal Growth & Design (2007), 7(6), 1007-1026.)

The present invention is directed, inter alia, to a salt that is (R)-8-chloro-1-methyl-2,3,4,5-tetrahydro-1H-3-benzazepine hydrochloride, Form IV. (R)-8-Chloro-1-methyl-2,3, 4,5-tetrahydro-1H-3-benzazepine hydrochloride, Form IV can be identified by its unique solid state signatures with respect to, for example, differential scanning calorimetry (DSC), X-ray powder diffraction (PXRD), and other solid state methods. Further characterization with respect to water or solvent content of the crystalline salts of the present invention can be gauged by any of the following methods for example, thermogravimetric analysis (TGA), DSC and the like. For DSC, it is known that the temperatures observed will depend upon sample purity, the rate of temperature change, as well as sample preparation technique and the particular instrument employed. Thus, the values reported herein relating to DSC thermograms can vary by about ±6° C. The values reported herein relating to DSC thermograms can also vary by about ±20 joules per gram. For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by about ±0.2000° 2θ. The relative intensities of the reported peaks can also vary. For TGA, the features reported herein can vary by about ±5° C. The TGA features reported herein can also vary by about ±2% weight change due to, for example, sample variation. Further characterization with respect to hygroscopicity of the crystalline salt can be gauged by, for example, dynamic moisture sorption (DMS). The DMS features reported herein can vary by about ±5% relative humidity. The DMS features reported herein can also vary by about ±5% weight change.

Compound 1 Hydrochloride Salt Form I.

Certain physical properties of Form I of Compound 1 hydrochloride salt are summarized in Table 1 below.

TABLE 1

| Compound 1 Hydrochloride Salt Form I | |
|---|---|
| DSC | FIG. 1: Endotherms with extrapolated onset temperatures at about 139° C. and about 199° C. |
| TGA | FIG. 1: Indicates non-solvated solid |
| PXRD | FIG. 2: Peaks of ≥13% relative intensity at 11.4557, 23.3357, 25.5265, 22.9715, 22.4406, 29.8412, 22.8674, 23.9054, 27.9943, 27.6833, 23.6019, 27.5885 °2θ |
| DMS | FIG. 3: Converts to Form III hemihydrate |

Certain X-ray powder diffraction peaks for Compound 1 hydrochloride salt Form I are shown in Table 2 below.

TABLE 2

| Pos. (°2θ) | Rel. Int. (%) |
|---|---|
| 5.0778 | 1.68 |
| 7.3192 | 4.69 |
| 10.2635 | 10.32 |
| 11.4557 | 100.00 |
| 12.3085 | 1.38 |
| 14.4847 | 9.80 |
| 15.1828 | 3.92 |
| 16.0298 | 10.28 |
| 18.3288 | 7.02 |
| 19.0025 | 6.59 |
| 19.6796 | 3.77 |
| 20.4689 | 9.90 |
| 21.6059 | 9.03 |
| 22.4406 | 23.93 |
| 22.8674 | 20.27 |
| 22.9715 | 24.84 |
| 23.3357 | 36.08 |
| 23.6019 | 13.13 |
| 23.9054 | 16.29 |

TABLE 2-continued

| Pos. (°2θ) | Rel. Int. (%) |
|---|---|
| 25.1999 | 10.34 |
| 25.5265 | 35.91 |
| 26.1210 | 4.42 |
| 27.2464 | 2.77 |
| 27.5885 | 13.02 |
| 27.6833 | 13.40 |
| 27.9943 | 13.65 |
| 28.4721 | 3.05 |
| 29.0145 | 3.68 |
| 29.8412 | 20.52 |
| 30.9185 | 6.38 |
| 31.2293 | 5.63 |
| 32.0266 | 5.17 |
| 32.5246 | 4.83 |
| 32.9329 | 4.28 |
| 34.2482 | 2.85 |
| 34.5812 | 5.30 |
| 36.4454 | 9.72 |
| 36.9131 | 2.73 |
| 37.6010 | 11.17 |
| 38.7499 | 2.41 |
| 39.3492 | 8.11 |
| 39.7576 | 3.85 |

By DSC, Compound 1 hydrochloride salt Form I displays an endothermic solid-solid phase transition with an onset temperature of ~140° C. at a heating rate of 10° C./min. With continued heating, the high-temperature form melted with degradation; the onset of melting was ~199° C., the same as the melting onset after dehydration of Compound 1 hydrochloride salt hemihydrate Form III.

The corresponding TGA scan shows the melting onset of the high-temperature form occurred after significant loss of sample weight (3.65%), while weight loss became more extreme after melting.

Compound 1 hydrochloride salt Form I absorbed enough water during DMS analysis for complete conversion to Compound 1 hydrochloride hemihydrate Form III, as confirmed by PXRD analysis.

Form I of Compound 1 hydrochloride salt can be prepared as described in Example 1.

Compound 1 Hydrochloride Salt Form II.

Certain physical properties of Form II of Compound 1 hydrochloride salt are summarized in Table 3 below.

TABLE 3

Figure 4:
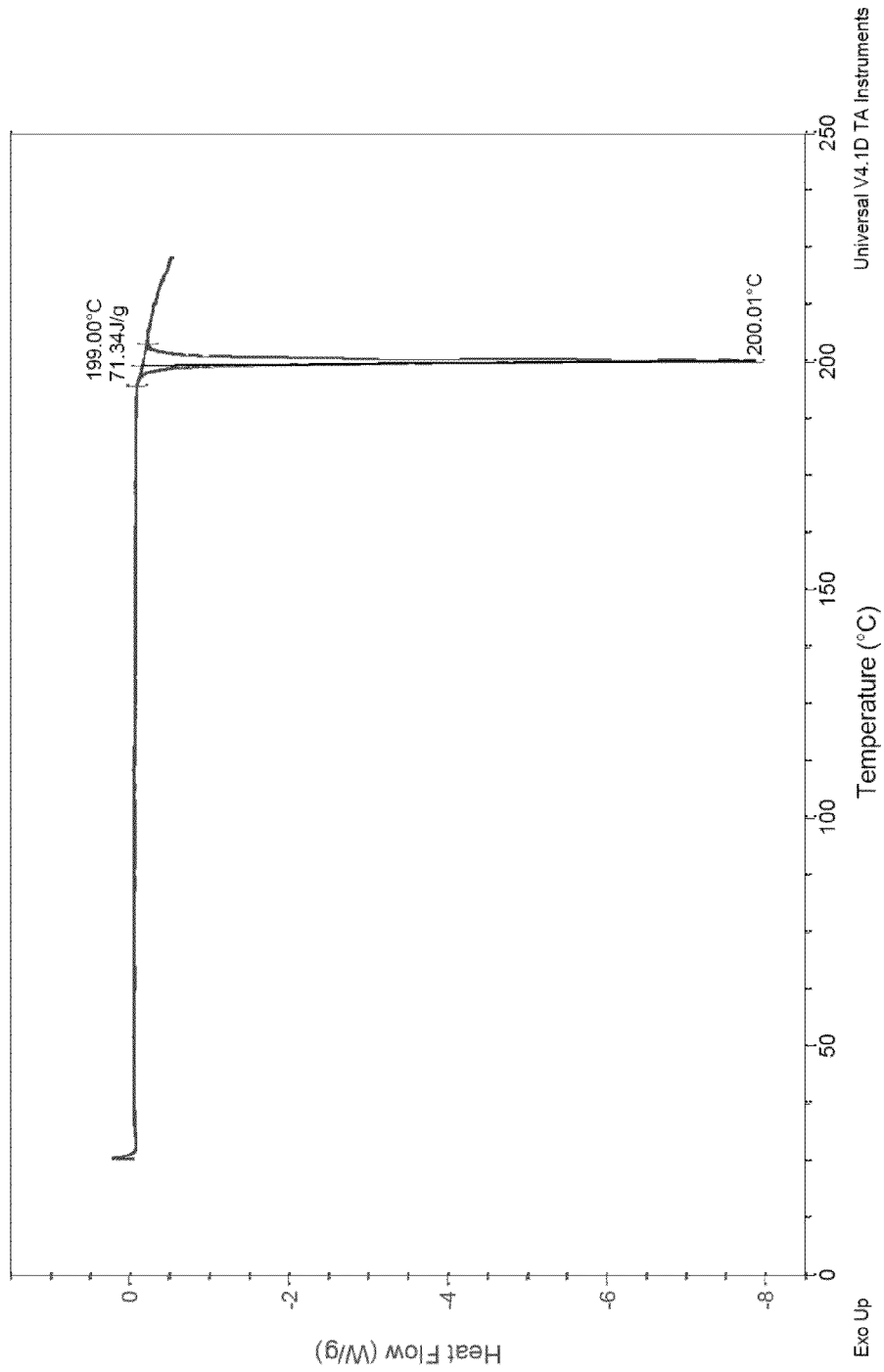
FIG. 4: DSC of Compound 1 Hydrochloride Salt Form II.

| | Compound 1 Hydrochloride Salt Form II |
|---|---|
| DSC | FIG. 4: Extrapolated onset temperature at about 199° C. |
| TGA | FIG. 5: Negligible weight loss below about 150° C. |
| PXRD | FIG. 6: Peaks at 12.9, 19.5, 19.8, 21.3, 21.6, 24.8, and 25.9 °2θ |
| DMS | FIG. 7: Converts to Form III hemihydrate |

Certain X-ray powder diffraction peaks for Compound 1 hydrochloride salt Form II are shown in Table 4 below.

TABLE 4

| Pos. (°2θ) |
|---|
| 6.5 |
| 9.6 |
| 10.2 |
| 12.9 |
| 17.1 |
| 17.5 |
| 17.8 |
| 18.5 |
| 19.5 |

TABLE 4-continued

| Pos. (°2θ) |
|---|
| 19.8 |
| 20.1 |
| 20.5 |
| 21.3 |
| 21.6 |
| 22.3 |
| 23.7 |
| 24.6 |
| 25.3 |
| 25.9 |
| 27.6 |
| 27.9 |
| 28.3 |
| 28.7 |
| 29.5 |
| 29.8 |
| 30.3 |
| 30.9 |
| 31.3 |
| 32.6 |
| 32.9 |

Figure 9:
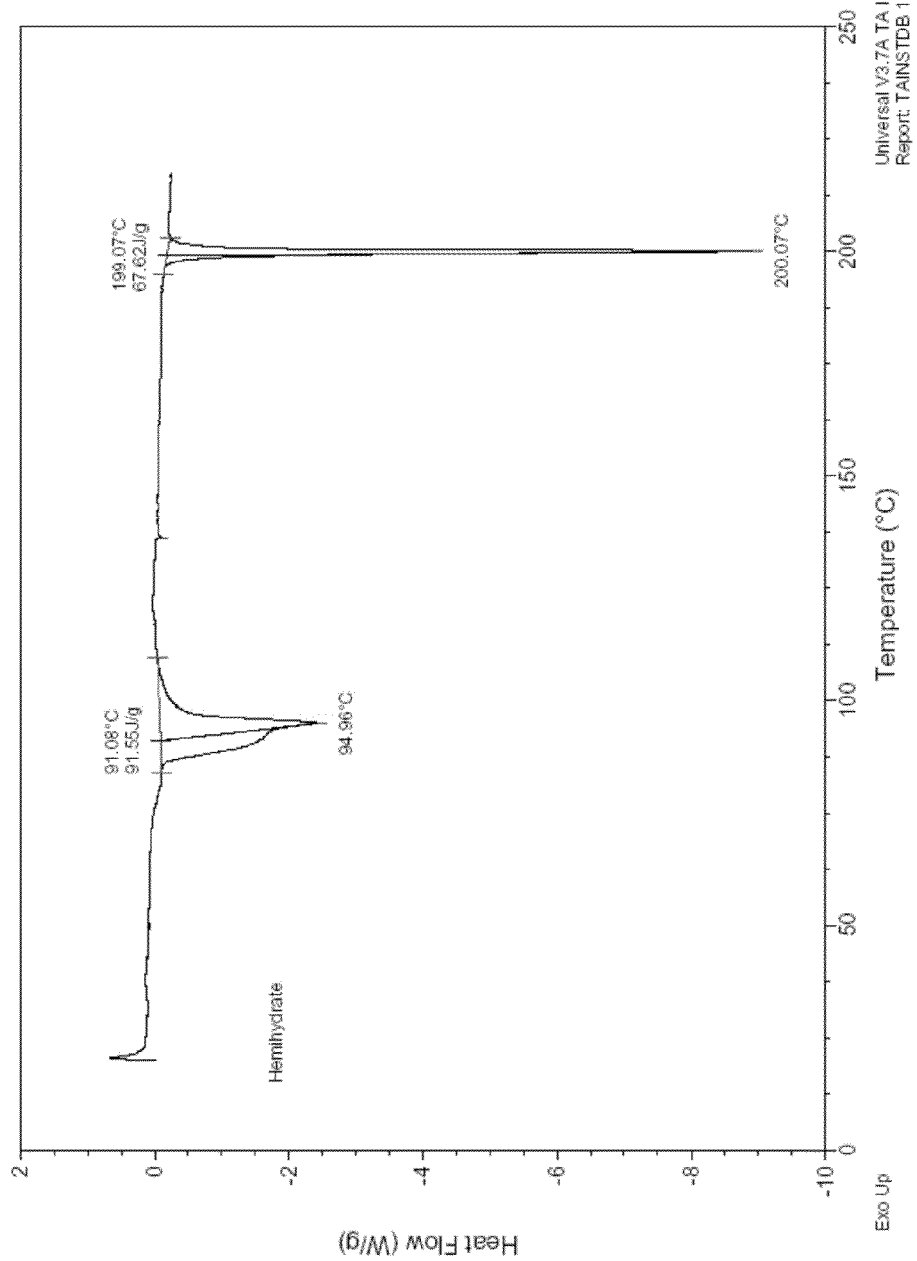
FIG. 9: DSC of Compound 1 Hydrochloride Salt Hemihydrate Form III.

DSC analysis of Compound 1 hydrochloride salt Form II (FIG. 4) confirms that it melted at the same onset temperature, 199° C., as the high-temperature form created by DSC analysis of Form I (FIG. 1), and the dehydrated form created by DSC analysis of hemihydrate Form III (FIG. 9).

DMS analysis shows that Compound 1 hydrochloride salt Form II behaved similarly to Form I, converting to the hemihydrate Form III, on the basis of mass gain, during the DMS scan.

Form II of Compound 1 hydrochloride salt can be prepared as described in Example 2.

Compound 1 Hydrochloride Salt Hemihydrate Form III.

Compound 1 hydrochloride salt hemihydrate Forms III is described in WO 2006/069363, which is incorporated herein by reference in its entirety.

Certain physical properties of Form III of Compound 1 hydrochloride salt hemihydrate are summarized in Table 5 below.

TABLE 5

Figure 8:
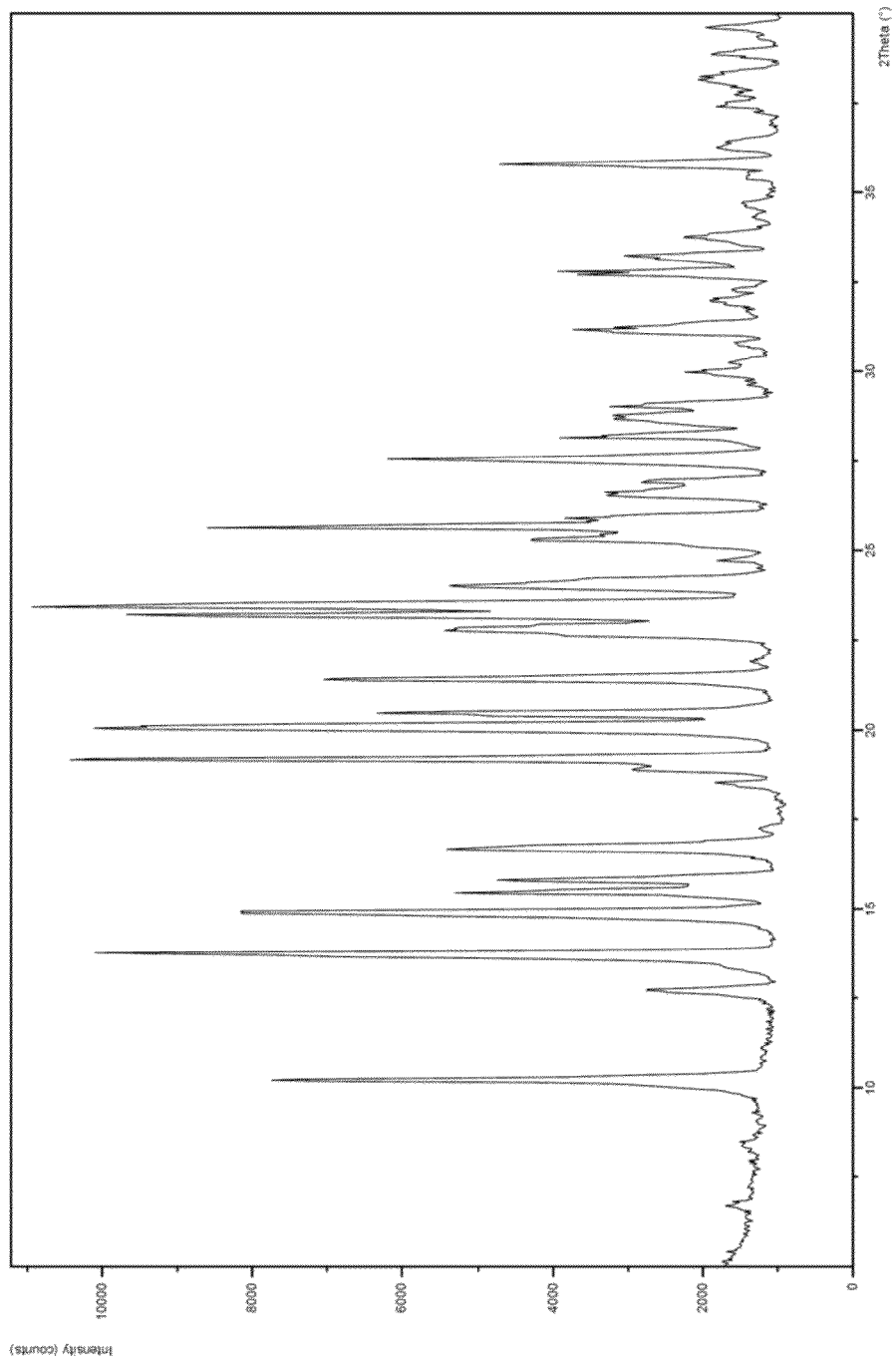
FIG. 8: PXRD of Compound 1 Hydrochloride Salt Hemihydrate Form III.

| | Compound 1 Hydrochloride Salt Hemihydrate, Form III |
|---|---|
| PXRD | FIG. 8: Peaks at 13.7°, 14.9°, 15.4°, 15.8°, 16.7°, 18.9 °2θ |
| DSC | FIG. 9: 95° C. (dehydration); 200° C. (melt) |
| TGA | FIG. 10: 3.7% water loss |
| DMS | FIG. 11: non-hygroscopic |

Compound 1 hydrochloride salt hemihydrate, Form III displays a dehydration feature calculated as a 3.7% weight loss which is consistent with the theoretical weight loss of 3.7% for a hemihydrate. Analysis by DSC further confirms the TGA results, where Compound 1 hydrochloride salt hemihydrate, Form III shows a dehydration event at about 95° C. and a melting/decomposition endotherm at about 200-201° C.

DMS data shows that Compound 1 hydrochloride salt hemihydrate, Form III is substantially non-hygroscopic, adsorbing less than 0.5 wt % water at 90% RH and the PXRD pattern showed no change in crystalline form of the salt after the DVS cycle.

Certain X-ray powder diffraction peaks for Compound 1 hydrochloride salt hemihydrate, Form III are shown in Table 6 below.

TABLE 6

| Pos. (°2θ) |
|---|
| 10.2 |
| 12.7 |
| 13.7 |
| 14.9 |
| 15.4 |
| 15.8 |
| 16.7 |
| 18.5 |
| 18.9 |
| 19.2 |
| 20.1 |
| 25.3 |
| 25.7 |
| 26.0 |
| 26.5 |
| 26.9 |
| 27.6 |
| 28.2 |
| 20.5 |
| 21.4 |
| 22.8 |
| 20.5 |
| 21.4 |
| 22.8 |
| 23.2 |
| 23.5 |
| 24.0 |
| 24.2 |
| 24.7 |
| 29.0 |
| 30.0 |
| 30.3 |
| 30.8 |
| 31.1 |
| 32.0 |
| 32.3 |
| 32.7 |
| 33.3 |
| 33.8 |
| 35.8 |

Form III of Compound 1 hydrochloride salt hemihydrate can be prepared as described in Example 3.

Compound 1 Hydrochloride Salt Form IV.

One aspect of the present invention pertains to (R)-8-chloro-1-methyl-2,3,4,5-tetrahydro-1H-3-benzazepine hydrochloride salt Form IV (Compound 1 hydrochloride salt Form IV). Certain physical properties of Form IV of Compound 1 hydrochloride salt are summarized in Table 7 below.

TABLE 7

Figure 12:
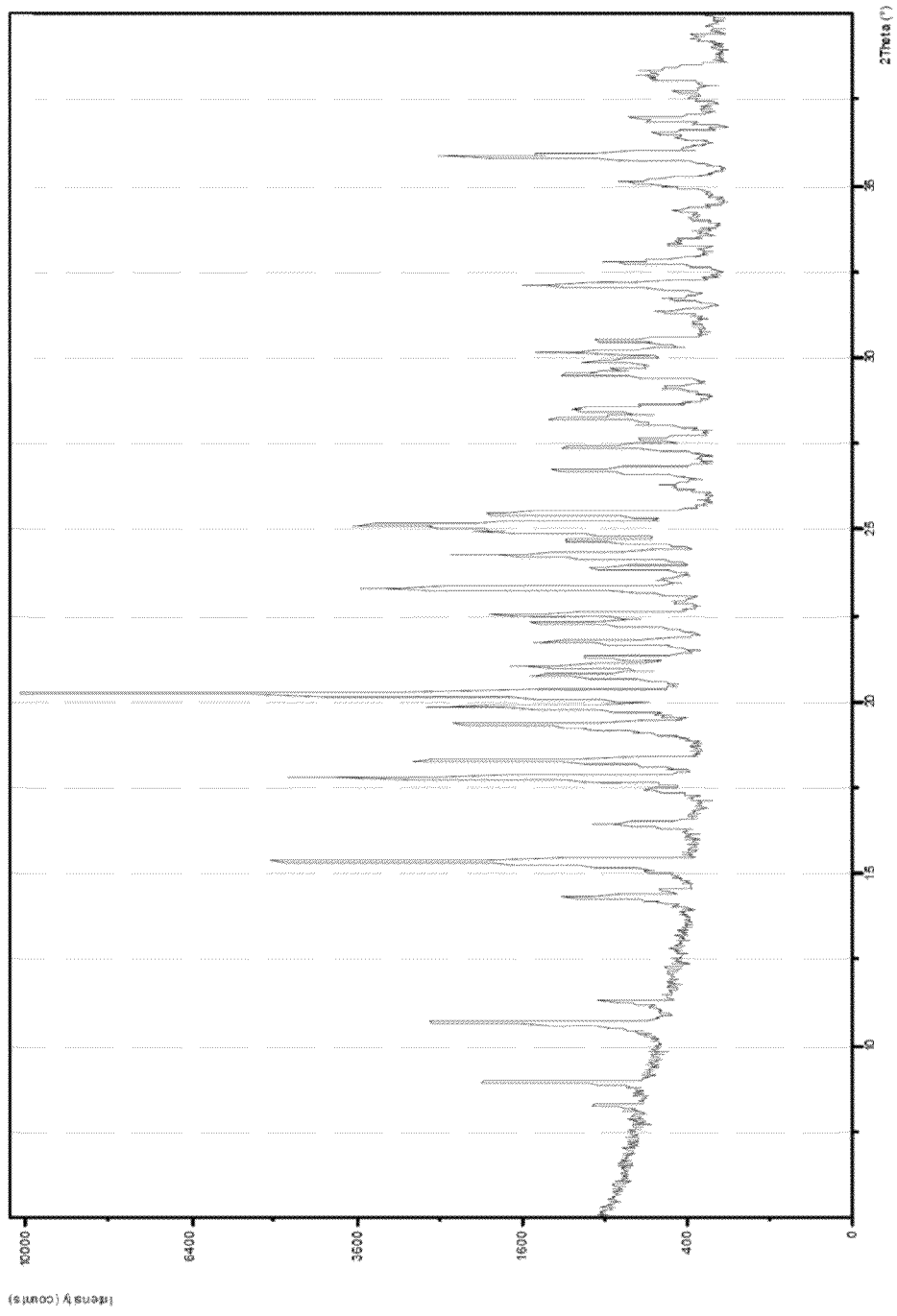
FIG. 12: PXRD of Compound 1 Hydrochloride Salt Form IV.

| | Compound 1 Hydrochloride Salt Form IV |
|---|---|
| PXRD | FIG. 12: Peaks of ≥19% relative intensity at 10.6724, 15.3400, 17.7719, 18.2736, 19.3300, 19.8388, 20.2316, 23.2759, 24.2509, 25.1334, and 35.8226 °2θ |
| DSC | FIG. 13: Endotherms with extrapolated onset temperatures at about 170° C. and about 199° C. |
| TGA | FIG. 13: Indicates non-solvated solid |
| DMS | FIG. 14: Converts to hemihydrate |

(R)-8-chloro-1-methyl-2,3,4,5-tetrahydro-1H-3-benzazepine hydrochloride salt Form IV, is an anhydrous polymorph. In 124 attempts, it did not crystallize from homogeneous supersaturated solution, but rather was prepared by solution-mediated phase transformation (SMPT) of other forms of (R)-8-chloro-1-methyl-2,3,4,5-tetrahydro-1H-3-benzazepine hydrochloride salt under near anhydrous conditions.

Compound 1 hydrochloride salt Form IV is the most stable of the three anhydrous polymorphs at ambient temperature, although it is not thermodynamically favored over the Compound 1 hydrochloride salt hemihydrate Form III, at % RH≥20. Compound 1 hydrochloride salt Form IV is enantiotropically related to Compound 1 hydrochloride salt Form II. The DSC result for Compound 1 hydrochloride salt Form IV shows an endothermic solid-to-solid phase transition to Form II occurring at 170° C. This is about 30° C. higher than the transition of Compound 1 hydrochloride salt Form I to Form II. However, the solid to solid phase-transition of Compound 1 hydrochloride salt from Form IV to Form II is highly dependent on heating rate. The endotherm observed at 170° C. is a kinetically-controlled transition, whereas the transition from Form IV to Form II under thermodynamic control occurs at about 80° C. to about 90° C.

The DSC result is consistent with Compound 1 hydrochloride salt Form IV being more stable than Compound 1 hydrochloride salt Form I at room temperature. This DSC result also suggests that Compound 1 hydrochloride salt Form IV has a monotropic relationship with Compound 1 hydrochloride salt Form I, which was confirmed by a competitive slurry of those forms at ambient temperature.

Figure 13:
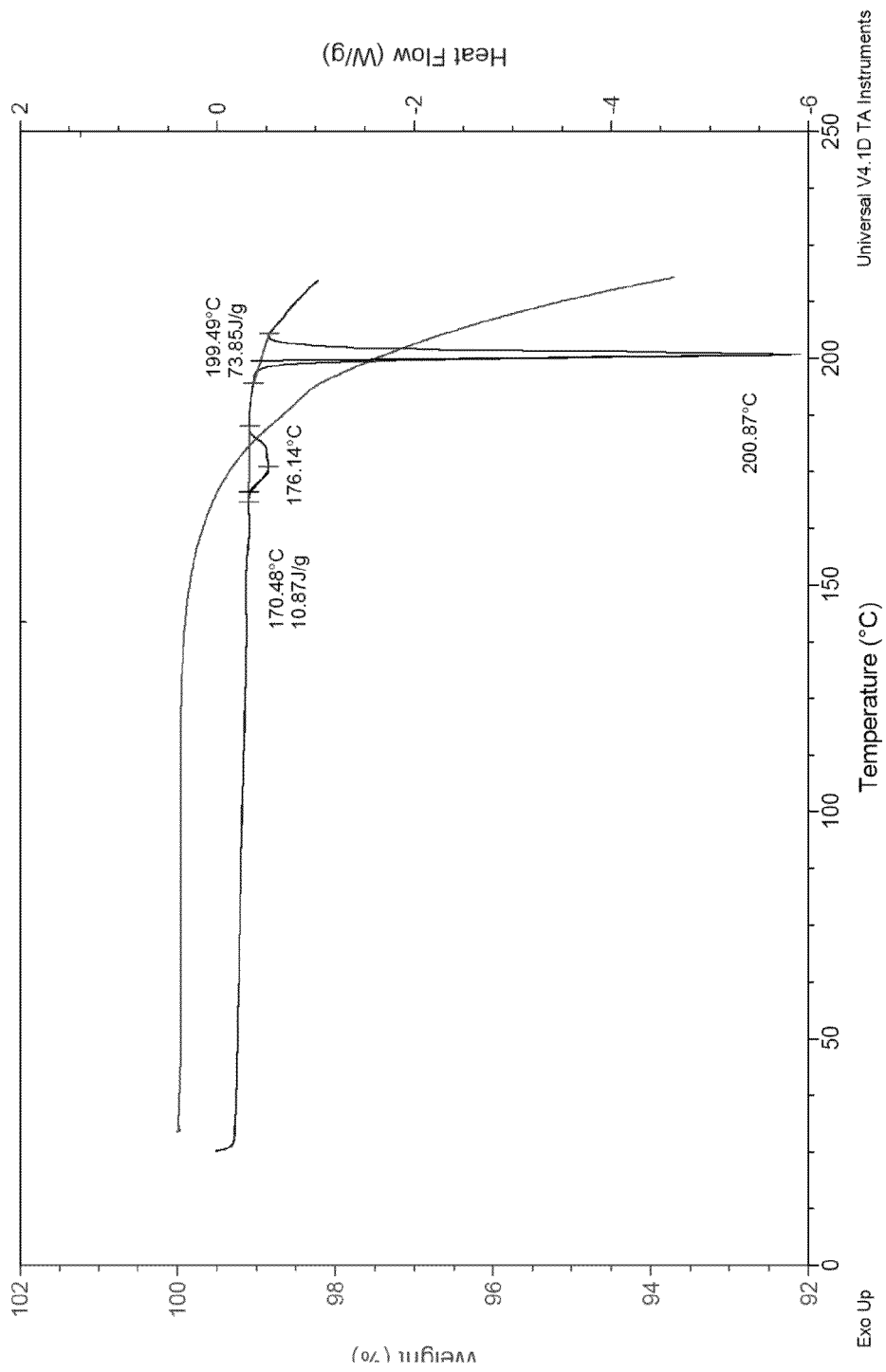
FIG. 13: DSC and TGA of Compound 1 Hydrochloride Salt Form IV.

The TGA result, overlaid with the DSC result in FIG. 13 shows that Compound 1 hydrochloride salt Form IV is a non-solvated solid.

Compound 1 hydrochloride salt Form IV behaved similarly to Compound 1 hydrochloride salt Forms I and II, converting to Compound 1 hydrochloride salt Form III on the basis of mass gain during the DMS scan.

Certain X-ray powder diffraction peaks for Compound 1 hydrochloride salt Form IV are shown in Table 8 below.

TABLE 8

| Pos. (°2θ) | Rel. Int. (%) |
|---|---|
| 8.2550 | 3.53 |
| 8.9354 | 14.92 |
| 10.6724 | 21.67 |
| 14.3140 | 8.42 |
| 15.3400 | 46.33 |
| 16.4348 | 6.28 |
| 17.7719 | 44.88 |
| 18.2736 | 24.57 |
| 19.3300 | 19.13 |
| 19.8388 | 22.61 |
| 20.2316 | 100.00 |
| 20.7400 | 11.24 |
| 21.0169 | 13.47 |
| 21.2700 | 6.80 |
| 21.7286 | 11.64 |
| 22.2800 | 11.17 |
| 22.5241 | 15.43 |
| 23.2759 | 30.15 |
| 23.8685 | 5.52 |
| 24.2509 | 19.33 |
| 24.6535 | 7.96 |
| 24.9200 | 17.11 |
| 25.1334 | 33.16 |
| 25.4534 | 16.57 |
| 26.7161 | 10.70 |
| 27.3771 | 9.46 |
| 28.2215 | 10.62 |
| 30.1400 | 10.94 |
| 30.4800 | 6.40 |
| 32.0918 | 12.97 |
| 35.8226 | 23.09 |

One aspect of the present invention is directed to a Compound 1 hydrochloride salt having an X-ray powder diffraction pattern comprising a peak, in terms of 2θ, at about 20.2316°. In some embodiments, the salt has an X-ray powder diffraction pattern comprising a peak, in terms of 2θ, at about 15.3400°. In some embodiments, the salt has an X-ray powder diffraction pattern comprising peaks, in terms of 2θ, at about 20.2316° and about 15.3400°. In some embodiments, the salt has an X-ray powder diffraction pattern comprising peaks, in terms of 2θ, at about 20.2316° and about 17.7719°. In some embodiments, the salt has an X-ray powder diffraction pattern comprising peaks, in terms of 2θ, at about 20.2316°, about 15.3400° and about 17.7719°. In some embodiments, the salt has an X-ray powder diffraction pattern comprising peaks, in terms of 2θ, at about 20.2316°, about 15.3400°, about 17.7719°, about 25.1334°, about 23.2759°, about 18.2736°, and about 35.8226°. In some embodiments, the salt has an X-ray powder diffraction pattern comprising peaks, in terms of 2θ, at about 20.2316°, about 15.3400°, about 17.7719°, about 25.1334°, about 23.2759°, about 18.2736°, about °, about 35.8226°, about 19.8388° and about 10.6724°. One aspect of the present invention is directed to a Compound 1 hydrochloride salt having an X-ray powder diffraction pattern comprising one or more peaks listed in Table 8. In some embodiments, the salt has an X-ray powder diffraction pattern substantially as shown in FIG. 12, wherein by "substantially" is meant that the reported peaks can vary by about ±0.2000° 2θ and also that the relative intensities of the reported peaks can vary.

In some embodiments, the Compound 1 hydrochloride salt has a differential scanning calorimetry thermogram comprising an endotherm with an extrapolated onset temperature between about 155° C. and about 185° C. In some embodiments, the Compound 1 hydrochloride salt has a differential scanning calorimetry thermogram comprising an endotherm with an extrapolated onset temperature at about 170° C.

In some embodiments, the Compound 1 hydrochloride salt has a differential scanning calorimetry thermogram comprising an endotherm with an extrapolated onset temperature between about 185° C. and about 215° C. In some embodiments, the Compound 1 hydrochloride salt has a differential scanning calorimetry thermogram comprising an endotherm with an extrapolated onset temperature at about 199° C.

In some embodiments, the Compound 1 hydrochloride salt has a differential scanning calorimetry thermogram comprising an endotherm with an extrapolated onset temperature between about 155° C. and about 185° C., and an endotherm with an extrapolated onset temperature between about 185° C. and about 215° C. In some embodiments, the Compound 1 hydrochloride salt has a differential scanning calorimetry thermogram comprising an endotherm with an extrapolated onset temperature at about 170° C., and an endotherm with an extrapolated onset temperature at about 199° C.

In some embodiments, the Compound 1 hydrochloride salt has a differential scanning calorimetry thermogram comprising an endotherm with an associated heat flow of about 11 joules per gram.

In some embodiments, the Compound 1 hydrochloride salt has a differential scanning calorimetry thermogram comprising an endotherm with an associated heat flow of about 74 joules per gram.

In some embodiments, the Compound 1 hydrochloride salt has a differential scanning calorimetry thermogram comprising an endotherm with an associated heat flow of about 11 joules per gram, and an endotherm with an associated heat flow of about 74 joules per gram.

In some embodiments, the Compound 1 hydrochloride salt has a thermogravimetric analysis profile substantially as shown in FIG. 13, wherein by "substantially" is meant that the reported TGA features can vary by about ±5° C. and by about ±2% weight change.

In some embodiments, the Compound 1 hydrochloride salt has a differential scanning calorimetry thermogram substantially as shown in FIG. 13, wherein by "substantially" is meant that the reported DSC features can vary by about ±6° C. and by about ±20 joules per gram.

Figure 14:
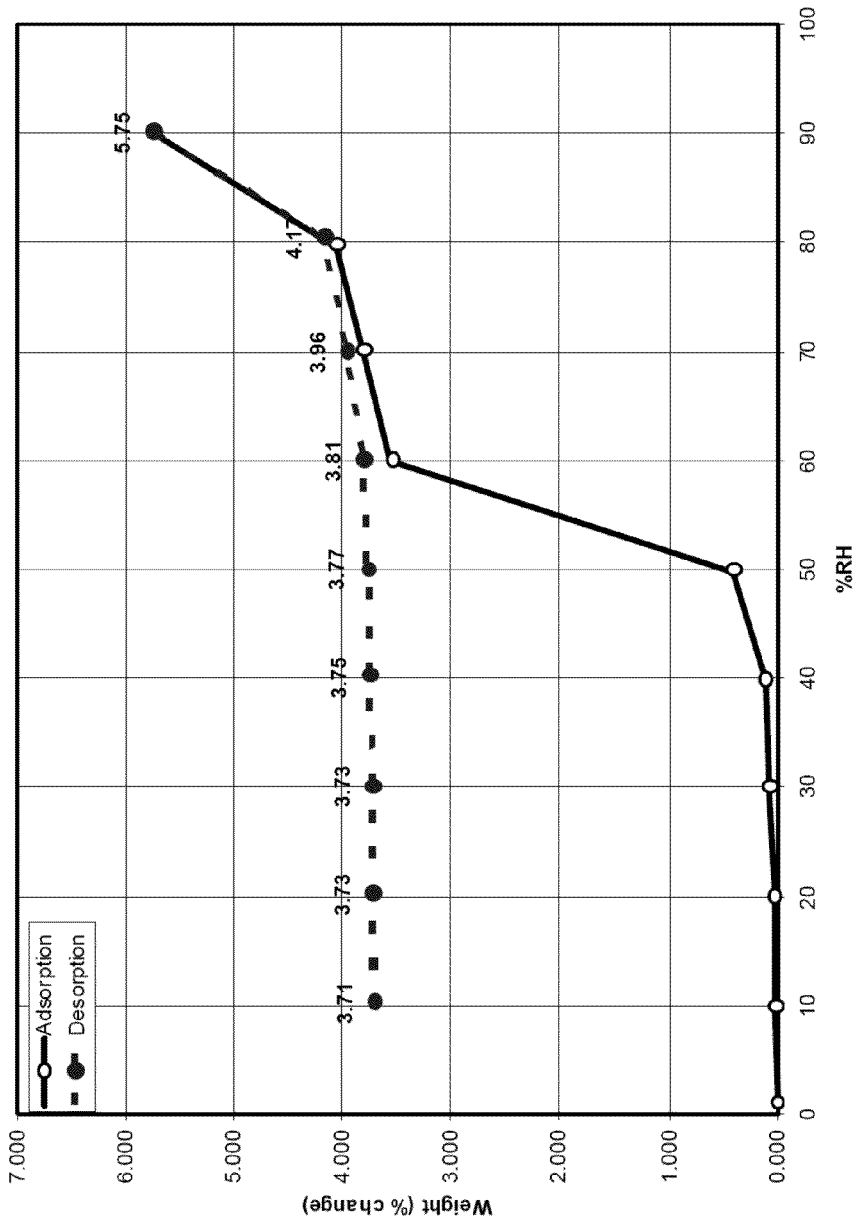
FIG. 14: DMS of Compound 1 Hydrochloride Salt Form IV.

In some embodiments, the Compound 1 hydrochloride salt has a dynamic moisture sorption profile substantially as shown in FIG. 14, wherein by "substantially" is meant that the reported DMS features can vary by about ±5% relative humidity and by about ±5% weight change.

Form IV of Compound 1 hydrochloride salt can be prepared by any of the suitable procedures known in the art for preparing crystalline polymorphs. In some embodiments Form IV of Compound 1 hydrochloride salt can be prepared as described in Example 4.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used in reference to salts described herein, it embraces pharmaceutically acceptable solvates and/or hydrates of such salts.

Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Hydrates and solvates can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Indications

In spite of the growing awareness of the health concerns linked to obesity, the percentage of individuals that are overweight or obese continues to increase. The most significant concern, from a public health perspective, is that children who are overweight grow up to be overweight or obese adults, and accordingly are at greater risk for major health problems. Therefore, it appears that the number of individuals that are overweight or obese will continue to increase.

As BMI increases for an individual there is an increased risk of morbidity and mortality relative to an individual with normal BMI. Accordingly, overweight and obese individuals (BMI of about 25 $kg/m^2$ and above) are at increased risk for physical ailments including, but not limited to, high blood pressure, cardiovascular disease (particularly hypertension), high blood cholesterol, dyslipidemia, type II (non-insulin dependent) diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), diseases of reproduction (such as sexual dysfunction, both male and female, including male erectile dysfunction), bladder control problems (such as stress incontinence), uric acid nephrolithiasis, psychological disorders (such as depression, eating disorders, distorted body image, and low self esteem).

The 5-$HT_{2C}$ receptor is recognized as a well-accepted receptor target for the treatment of obesity, psychiatric, and other disorders. See, for example, Halford et al., *Serotonergic Drugs Effects on Appetite Expression and Use for the Treatment of Obesity*, Drugs 2007; 67 (1): 27-55; Naughton et al., *A Review Of The Role Of Serotonin Receptors In Psychiatric Disorders*. Human Psychopharmacology (2000), 15(6), 397-415.

In addition to obesity, the 5-$HT_{2C}$ receptor is also involved in other diseases, conditions and disorders, such as, obsessive compulsive disorder, some forms of depression, and epilepsy. Accordingly, 5-$HT_{2C}$ receptor agonists can have anti-panic properties, and properties useful for the treatment of sexual dysfunction. In addition, 5-$HT_{2C}$ receptor agonists are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. What the individual is doing with regard to food and weight is neither normal nor healthy.

The 5-$HT_{2C}$ receptor plays a role in Alzheimer Disease (AD). Therapeutic agents currently prescribed for Alzheimer's disease (AD) are cholinomimetic agents that act by inhibiting the enzyme acetylcholinesterase. The resulting effect is increased levels of acetylcholine, which modestly improves neuronal function and cognition in patients with AD. Although, dysfunction of cholinergic brain neurons is an early manifestation of AD, attempts to slow the progression of the disease with these agents have had only modest success, perhaps because the doses that can be administered are limited by peripheral cholinergic side effects, such as tremors, nausea, vomiting, and dry mouth. In addition, as AD progresses, these agents tend to lose their effectiveness due to continued cholinergic neuronal loss.

Therefore, there is a need for agents that have beneficial effects in AD, particularly in alleviating symptoms by improving cognition and slowing or inhibiting disease progression, without the side effects observed with current therapies. Therefore, serotonin 5-$HT_{2C}$ receptors, which are exclusively expressed in brain, are attractive targets.

Another disease, disorder or condition that can is associated with the function of the 5-$HT_{2C}$ receptor is erectile dysfunction (ED). Erectile dysfunction is the inability to achieve or maintain an erection sufficiently rigid for intercourse, ejaculation, or both. An estimated 20-30 million men in the United States have this condition at some time in their lives. The prevalence of the condition increases with age. Five percent of men 40 years of age report ED. This rate increases to between 15% and 25% by the age of 65, and to 55% in men over the age of 75 years.

Erectile dysfunction can result from a number of distinct problems. These include loss of desire or libido, the inability to maintain an erection, premature ejaculation, lack of emission, and inability to achieve an orgasm. Frequently, more than one of these problems presents themselves simultaneously. The conditions may be secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems. Erectile dysfunction, when organic, is primarily due to vascular irregularities associated with atherosclerosis, diabetes, and hypertension.

There is evidence for use of a serotonin 5-$HT_{2C}$ agonist for the treatment of sexual dysfunction in males and females. The serotonin 5-$HT_{2C}$ receptor is involved with the processing and integration of sensory information, regulation of central monoaminergic systems, and modulation of neuroendocrine responses, anxiety, feeding behavior, and cerebrospinal fluid production [Tecott, L. H., et al. Nature 374: 542-546 (1995)]. In addition, the serotonin 5-$HT_{2C}$ receptor has been implicated in the mediation of penile erections in rats, monkeys, and humans.

In summary, the 5-$HT_{2C}$ receptor is a validated and well-accepted receptor target for the prophylaxis and/or treatment of 5-$HT_{2C}$ mediated receptor diseases and disorders, such as, obesity, eating disorders, psychiatric disorders, Alzheimer Disease, sexual dysfunction and disorders related thereto. It can be seen that there exists a need for selective 5-$HT_{2C}$ receptor agonists that can safely address these needs. The present invention is directed to these, as well as other, important ends.

One aspect of the present invention pertains to methods for weight management, comprising administering to an individual in need thereof, a therapeutically effective amount of a salt, a composition, or a pharmaceutical composition of the present invention.

In some embodiments, the weight management comprises weight loss.

In some embodiments, the weight management comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index $\geq 30$ kg/m$^2$.

In some embodiments, the individual in need of weight management is an overweight patient with an initial body mass index $\geq 27$ kg/m$^2$ in the presence of at least one weight related comorbid condition.

In some embodiments, the individual in need of weight management is an overweight patient with an initial body mass index $\geq 27$ kg/m$^2$ in the presence of at least one weight related comorbid condition selected from: hypertension, dyslipidemia, cardiovascular disease, glucose intolerance, and sleep apnea.

In some embodiments, the method further comprises administering phentermine to the individual.

One aspect of the present invention pertains to uses of a salt of the present invention, in the manufacture of a medicament for weight management in an individual.

In some embodiments, the weight management comprises weight loss.

In some embodiments, the weight management comprises maintenance of weight loss.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual is an obese patient with an initial body mass index ≥30 kg/m$^2$.

In some embodiments, the individual is an overweight patient with an initial body mass index ≥27 kg/m$^2$ in the presence of at least one weight related comorbid condition.

In some embodiments, the individual is an overweight patient with an initial body mass index ≥27 kg/m$^2$ in the presence of at least one weight related comorbid condition selected from: hypertension, dyslipidemia, cardiovascular disease, glucose intolerance, and sleep apnea.

In some embodiments, the medicament for weight management is used in combination with phentermine.

One aspect of the present invention pertains to salts, compositions, and pharmaceutical compositions of the present invention, for use in a method of treatment of the human or animal body by therapy.

One aspect of the present invention pertains to salts, compositions, and pharmaceutical compositions of the present invention, for use in a method of weight management. One aspect of the present invention pertains to salts, compositions, and pharmaceutical compositions of the present invention, for use in a method of weight loss.

One aspect of the present invention pertains to salts, compositions, and pharmaceutical compositions of the present invention, for use in a method of maintenance of weight loss.

One aspect of the present invention pertains to salts, compositions, and pharmaceutical compositions of the present invention, for use in a method of weight management further comprising a reduced-calorie diet.

One aspect of the present invention pertains to salts, compositions, and pharmaceutical compositions of the present invention, for use in a method of weight management further comprising a program of regular exercise.

One aspect of the present invention pertains to salts, compositions, and pharmaceutical compositions of the present invention, for use in a method of weight management further comprising a reduced-calorie diet and a program of regular exercise.

One aspect of the present invention pertains to salts, compositions, and pharmaceutical compositions of the present invention, for use in a method of weight management in an obese patient with an initial body mass index ≥30 kg/m$^2$.

One aspect of the present invention pertains to salts, compositions, and pharmaceutical compositions of the present invention, for use in a method of weight management in an overweight patient with an initial body mass index ≥27 kg/m$^2$ in the presence of at least one weight related co-morbid condition.

One aspect of the present invention pertains to salts, compositions, and pharmaceutical compositions of the present invention, for use in a method of weight management in an overweight patient with an initial body mass index ≥27 kg/m$^2$ in the presence of at least one weight related co-morbid condition selected from: hypertension, dyslipidemia, cardiovascular disease, glucose intolerance, and sleep apnea.

One aspect of the present invention pertains to salts, compositions, and pharmaceutical compositions of the present invention, for use in a method of weight management in combination with phentermine Pharmaceutical Compositions Medicaments, or pharmaceutical compositions, may be prepared by any suitable method, typically by uniformly mixing the active compound(s) with liquids or finely divided solid carriers, or both, in the required proportions and then, if necessary, forming the resulting mixture into a desired shape.

The crystalline salts described herein and physiologically functional derivatives thereof can be used as active ingredients in pharmaceutical compositions, specifically as 5-HT$_{2C}$ receptor agonists for treating disorders ameliorated by agonizing the 5-HT$_{2C}$ receptor. The term "active ingredient" as defined in the context of a "pharmaceutical composition" is intended to mean a component of a pharmaceutical composition that provides the primary pharmacological effect, as opposed to an "inactive ingredient" which would generally be recognized as providing no pharmaceutical benefit.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A crystalline salt described herein can be formulated into a pharmaceutical composition using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that a crystalline salt described herein may be administered as a raw or pure chemical for use in method treatment of the present invention, it is preferable however to present the active pharmaceutical ingredient as a pharmaceutical formulation or composition further comprising a pharmaceutically acceptable carrier.

The invention thus further provides methods of using pharmaceutical formulations comprising a crystalline salt described herein, together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimum degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compositions described herein, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compositions or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

The dose when using the compositions described herein can vary within wide limits and as is customary and is known to the physician, it is to be tailored to the individual conditions in each individual case. It depends, for example, on the nature and severity of the illness to be treated, on the condition of the patient, on the active pharmaceutical ingredient employed or on whether an acute or chronic disease state is treated or prophylaxis is conducted or on whether further active compositions are administered in addition to the compositions described herein. Representative doses include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example two, three or four doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular active pharmaceutical ingredient employed, whether a drug delivery system is utilized, on whether an acute or chronic disease state is being treated or prophylaxis is conducted or on whether further active compositions are administered in addition to the compositions of the present invention and as part of a drug combination. The dosage regimen for treating a disease condition with the compositions and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example two-, three- or four-part administrations. If appropriate, depending on individual behavior, it may be necessary to deviate upward or downward from the daily dose indicated.

The compositions described herein can be administrated in a wide variety of oral and parenteral dosage forms. It will be obvious to those skilled in the art that the following dosage forms may comprise an active pharmaceutical ingredient of the invention.

For preparing pharmaceutical compositions from the crystalline salts described herein, the pharmaceutically acceptable carriers can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted to the desire shape and size. The powders and tablets may contain varying percentage amounts of the active pharmaceutical ingredient. A representative amount in a powder or tablet may contain from 0.5 to about 90 percent of the active pharmaceutical ingredient; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like.

Preparing pharmaceutical compositions optionally includes the formulation of the active pharmaceutical ingredient with an encapsulating material as a carrier thus providing a capsule in which the active component, with or without further carriers, is surrounded by and in association with a carrier.

Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions described herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compositions described herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compositions of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the pharmaceutical compositions of the present invention as an aerosol can be prepared by processes well known to the person skilled in the art. For their preparation, for example, solutions or dispersions of the pharmaceutical compositions of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the active pharmaceutical ingredient will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the active pharmaceutical ingredient in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Pharmaceutical compositions for "combination-therapy" may be prepared by admixing at least two pharmaceutical agents described herein and a pharmaceutically acceptable carrier.

It is noted that when selective 5-HT$_{2C}$ receptor agonists are utilized as active ingredients in pharmaceutical compositions, these are not intended for use only in humans, but in other non-human animals as well. Indeed, recent advances in the area of animal health-care mandate that consideration be given for the use of active agents, such as selective 5-HT$_{2C}$ receptor agonists, for the treatment of disorders ameliorated by reduction of norepinephrine level in companionship animals (e.g., cats, dogs, etc.) and in livestock animals (e.g., cows, chickens, fish, etc.) Those of ordinary skill in the art are readily credited with understanding the utility of such active pharmaceutical ingredients in such settings.

Other Utilities

The present disclosure includes all isotopes of atoms occurring in the present crystalline salts. Isotopes include those atoms having the same atomic number but different mass numbers. One aspect of the present invention includes every combination of one or more atoms in the present crystalline salts that is replaced with an atom having the same atomic number but a different mass number. One such example is the replacement of an atom that is the most naturally abundant isotope, such as $^1$H or $^{12}$C, found in one of the present crystalline salts, with a different atom that is not the most naturally abundant isotope, such as $^2$H or $^3$H (replacing $^1$H), or $^{11}$C, $^{13}$C, or $^{14}$C (replacing $^{12}$C). A crystalline salts wherein such a replacement has taken place is commonly referred to as being isotopically-labeled. Isotopic-labeling of the present crystalline salts can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$C. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present crystalline salts, wherein the naturally occurring distribution of the isotopes in the composition is perturbed. Another aspect of the present invention includes compositions and pharmaceutical compositions comprising crystalline salts as described herein wherein the crystalline salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled crystalline salts of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Examples infra, by substituting an isotopically labeled reagent for a non-isotopically labeled reagent. Other synthetic methods that are useful are discussed infra. Moreover, it should be understood that all of the atoms represented in the crystalline salts of the invention can be either the most commonly occurring isotope of such atoms or a scarcer radio-isotope or non-radioactive isotope.

Synthetic methods for incorporating radio-isotopes into organic compounds are applicable to crystalline salts of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Other uses of the disclosed crystalline salts and methods will become apparent to those skilled in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting. Those of skill in the art will readily recognize a variety of noncritical parameters which can be changed or modified to yield essentially the same results.

EXAMPLES

The following examples are provided to further define the invention without, however, limiting the invention to the particulars of these examples. The crystalline salts described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Powder X-ray Diffraction (PXRD) studies were conducted using an X'Pert PRO MPD powder diffractometer (PANalytical, Inc.) with a Cu source set at 45 kV and 40 mA, Cu(Kα) radiation and an X'Celerator detector. Samples were placed on a PXRD sample plate either as-is or ground slightly to reduce the size of large particles or crystals. Data were collected with the samples spinning from 5° to 40° 2θ. Data were analyzed by X'Pert Data Viewer software, version 1.0a, to determine crystallinity and/or crystal form, and by X'Pert HighScore software, version 1.0b, to generate the tables of PXRD peaks.

Differential scanning calorimetry (DSC) studies were conducted using a TA Instruments, Q2000 at heating rate 10° C./min from ~25° C. to ~220° C. The instruments were calibrated by the vendor for temperature and energy using the melting point and enthalpy of fusion of an indium standard.

Thermogravimetric analyses (TGA) were conducted using a TA Instruments TGA Q5000 at heating rate 10° C./min. The instrument was calibrated by the vendor using Alumel and Nickel Curie points for the furnace temperature and a standard weight for the balance.

Dynamic moisture-sorption (DMS) studies were conducted using a dynamic moisture-sorption analyzer, VTI Corporation, SGA-100. Samples were prepared for DMS analysis by placing 5 mg to 20 mg of a compound or a salt thereof in a tared sample holder. The sample was placed on the hang-down wire of the VTI balance. A drying step was run, typically at 40° C. and 0.5-1% RH for 1-2 h. The isotherm temperature is 25° C. Defined % RH holds typically ranged from 10% RH to 90% RH or 95% RH, with intervals of 10 to 20% RH. A % weight change smaller than 0.010% over a specified number of minutes (typically 10-20), or up to 2 h, whichever occurs first, is required before continuing to the next % RH hold. The water content of the sample equilibrated as described above was determined at each % RH hold.

Example 1

Preparation of (R)-8-Chloro-1-methyl-2,3,4,5-tetrahydro-1H-3-benzazepine Hydrochloride Salt Form I (Compound 1 Hydrochloride Salt Form I)

Method 1

The title salt was crystallized from homogeneous solutions of Compound 1 hydrochloride salt in ethanol, n-propyl alcohol, isopropyl alcohol, acetonitrile, or acetone, under anhydrous conditions at ambient temperature by fast evaporation.

Method 2

The title salt was crystallized from homogeneous solutions of Compound 1 hydrochloride salt in ethanol, chloroform, isopropyl alcohol, acetonitrile, or acetone, under anhydrous conditions at ambient temperature by slow evaporation.

Method 3

The title salt was crystallized by the addition of ethyl acetate, toluene, or hexanes to a saturated solution of Compound 1 hydrochloride salt in dichloromethane, chloroform, methanol, ethanol, or tetrahydrofuran.

Method 3

The title salt was crystallized by the addition of a saturated solution of Compound 1 hydrochloride salt in dichloromethane or chloroform, to ethyl acetate, toluene, cumene, or hexanes.

Method 5

The title salt was prepared by solution-mediated phase transformation of Compound 1 hydrochloride salt Form II or Compound 1 hydrochloride salt hemihydrate Form III, in an anhydrous solvent at ≤44° C., with isolation of Compound 1 hydrochloride salt Form I before further transformation to Compound 1 hydrochloride salt Form IV.

Figure 2:
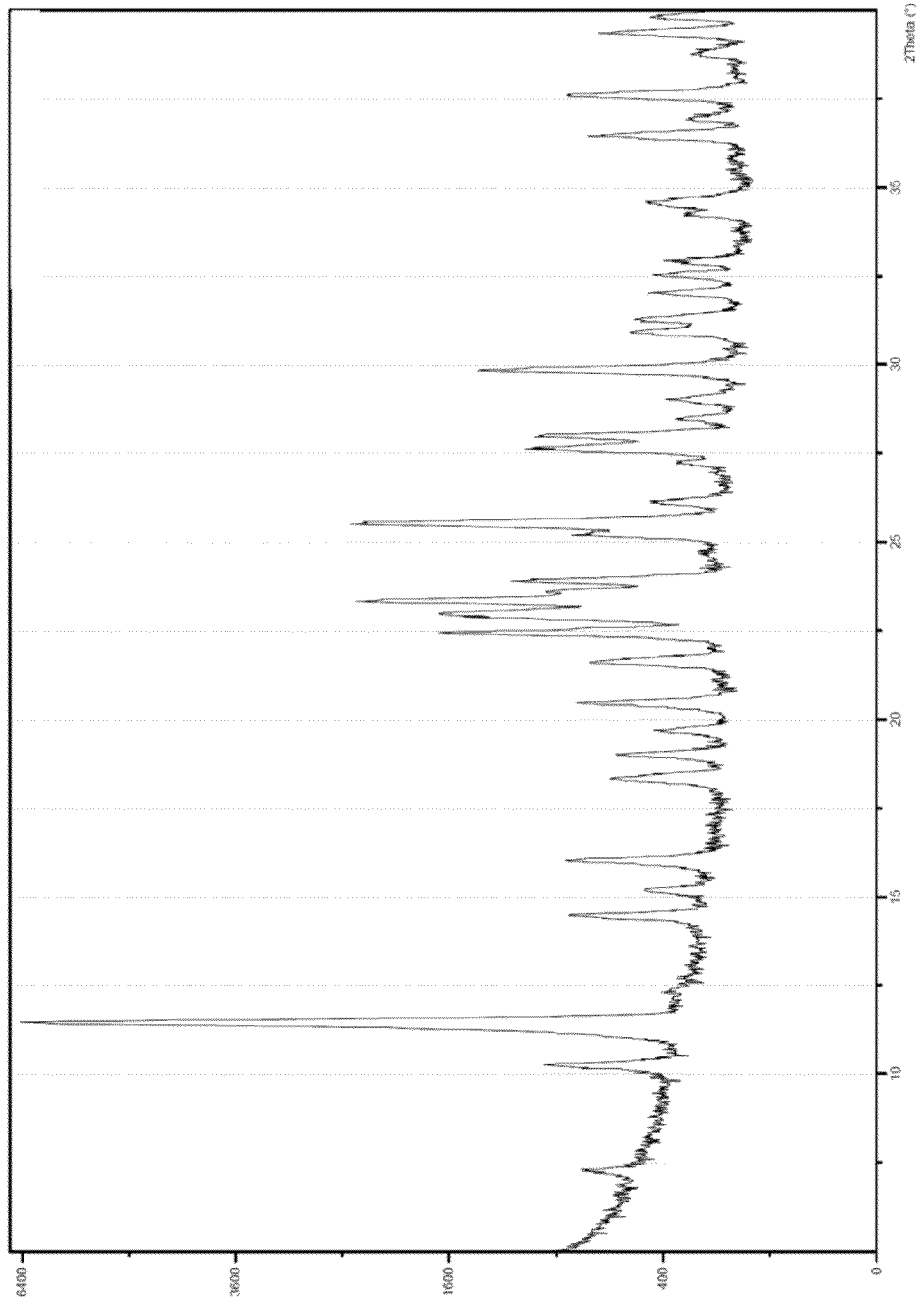
FIG. 2: PXRD of Compound 1 Hydrochloride Salt Form I.
Figure 3:
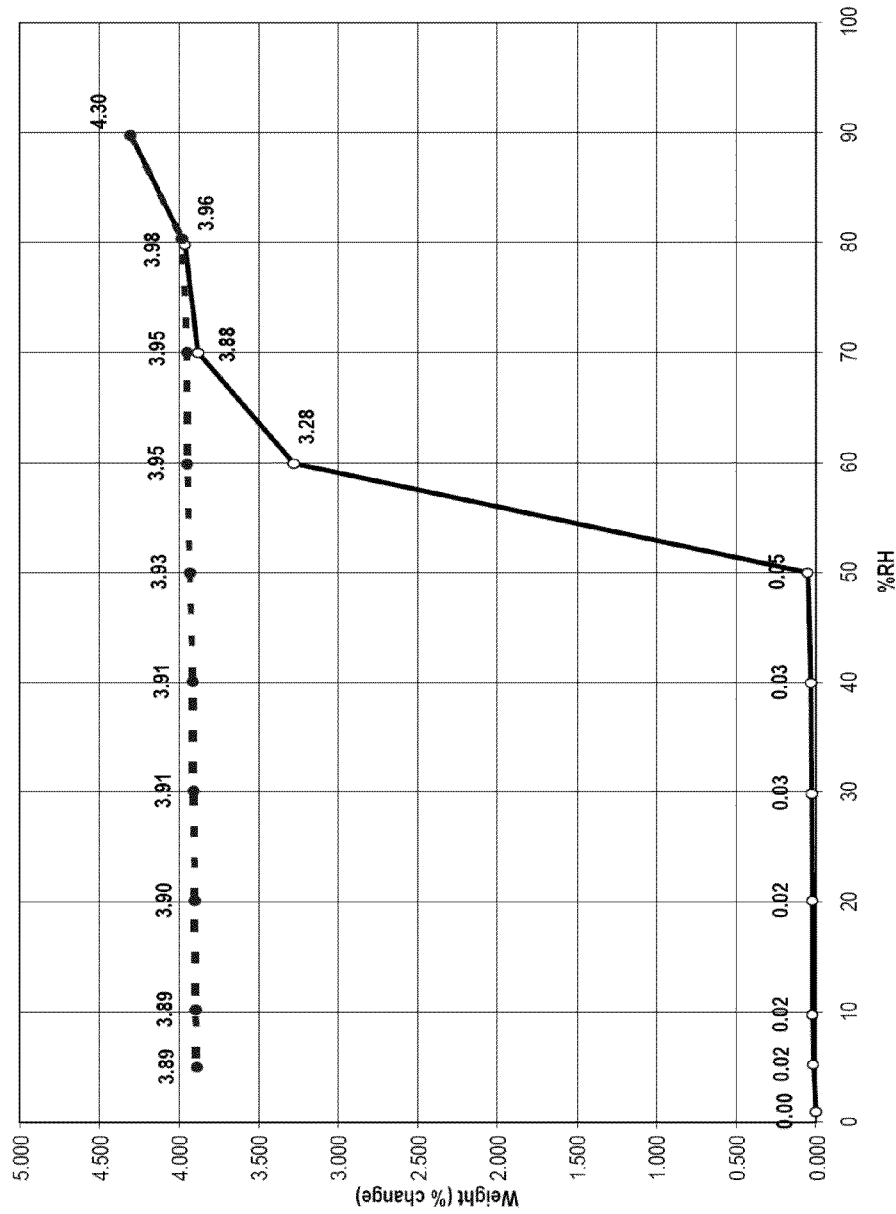
FIG. 3: DMS of Compound 1 Hydrochloride Salt Form I.

DSC and TGA analyses of the title salt are shown in FIG. 1. The powder X-ray diffraction pattern of the title salt is shown in FIG. 2. DMS analysis of the title salt is shown in FIG. 3.

Example 2

Preparation of (R)-8-Chloro-1-methyl-2,3,4,5-tetrahydro-1H-3-benzazepine Hydrochloride Salt Form II (Compound 1 Hydrochloride Salt Form II)

Method 1

The title salt was crystallized from homogeneous solutions of Compound 1 hydrochloride salt in ethanol, toluene, ethyl acetate, dichloromethane, tetrahydrofuran or isopropyl alcohol, under anhydrous conditions by fast cooling to ~0° C. from 10-15° C. below the respective boiling points of the solvents.

Method 2

The title salt was crystallized from homogeneous solutions of Compound 1 hydrochloride salt in ethanol, n-propanol, acetonitrile, toluene, ethyl acetate, butanone or methyl isobutyl ketone, under anhydrous conditions by slow cooling to 10° C. from 10-15° C. below the respective boiling points of the solvents.

Method 3

The title salt was prepared by dehydration of Compound 1 hydrochloride salt hemihydrate Form III at temperatures near or above 90° C.

Method 4

The title salt was prepared by solution-mediated phase transformation of Compound 1 hydrochloride salt Form I, Compound 1 hydrochloride salt Form IV, or Compound 1 hydrochloride salt hemihydrate Form III, in an anhydrous solvent at ≥90° C.

Figure 5:
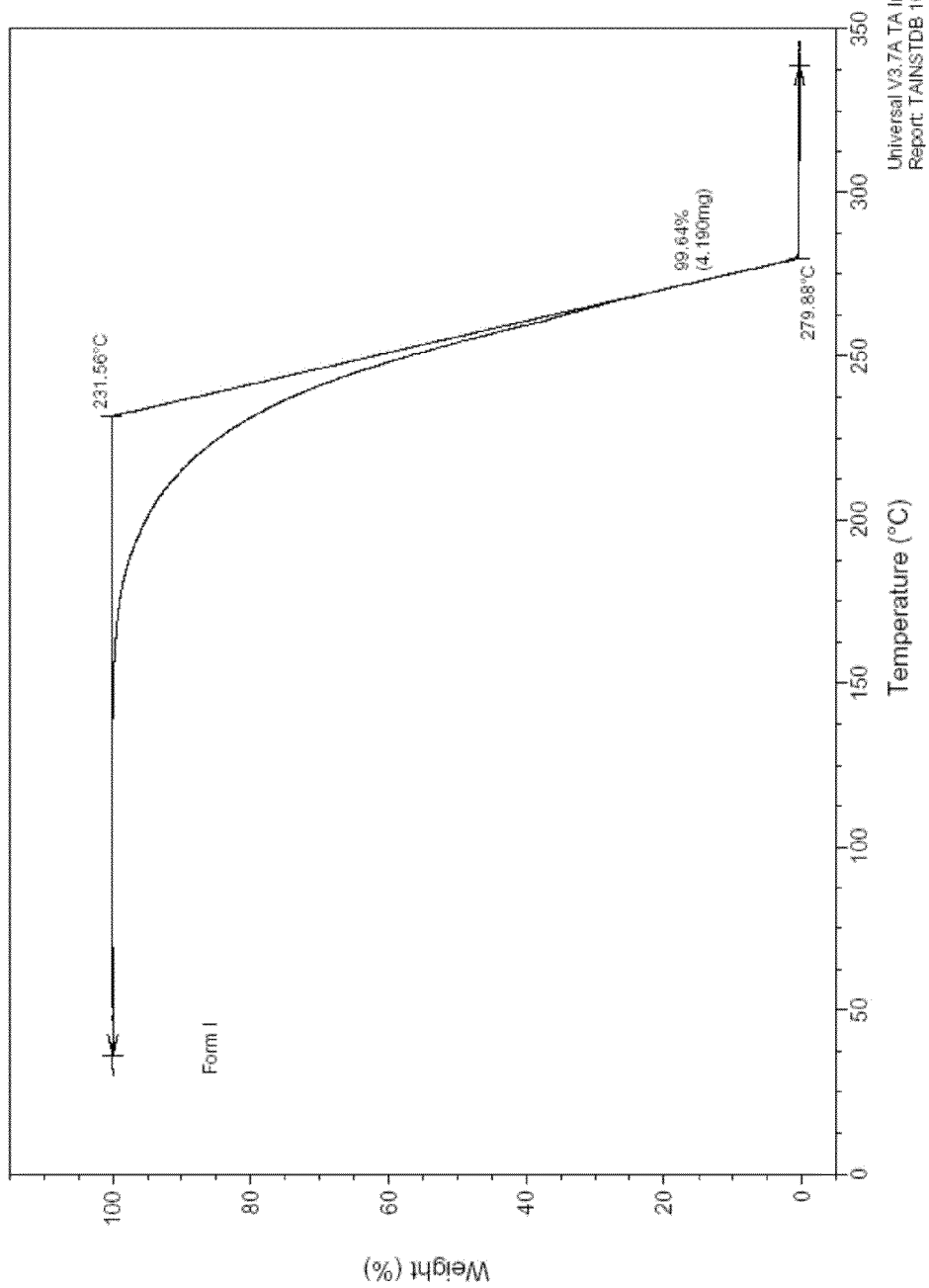
FIG. 5: TGA of Compound 1 Hydrochloride Salt Form II.
Figure 6:
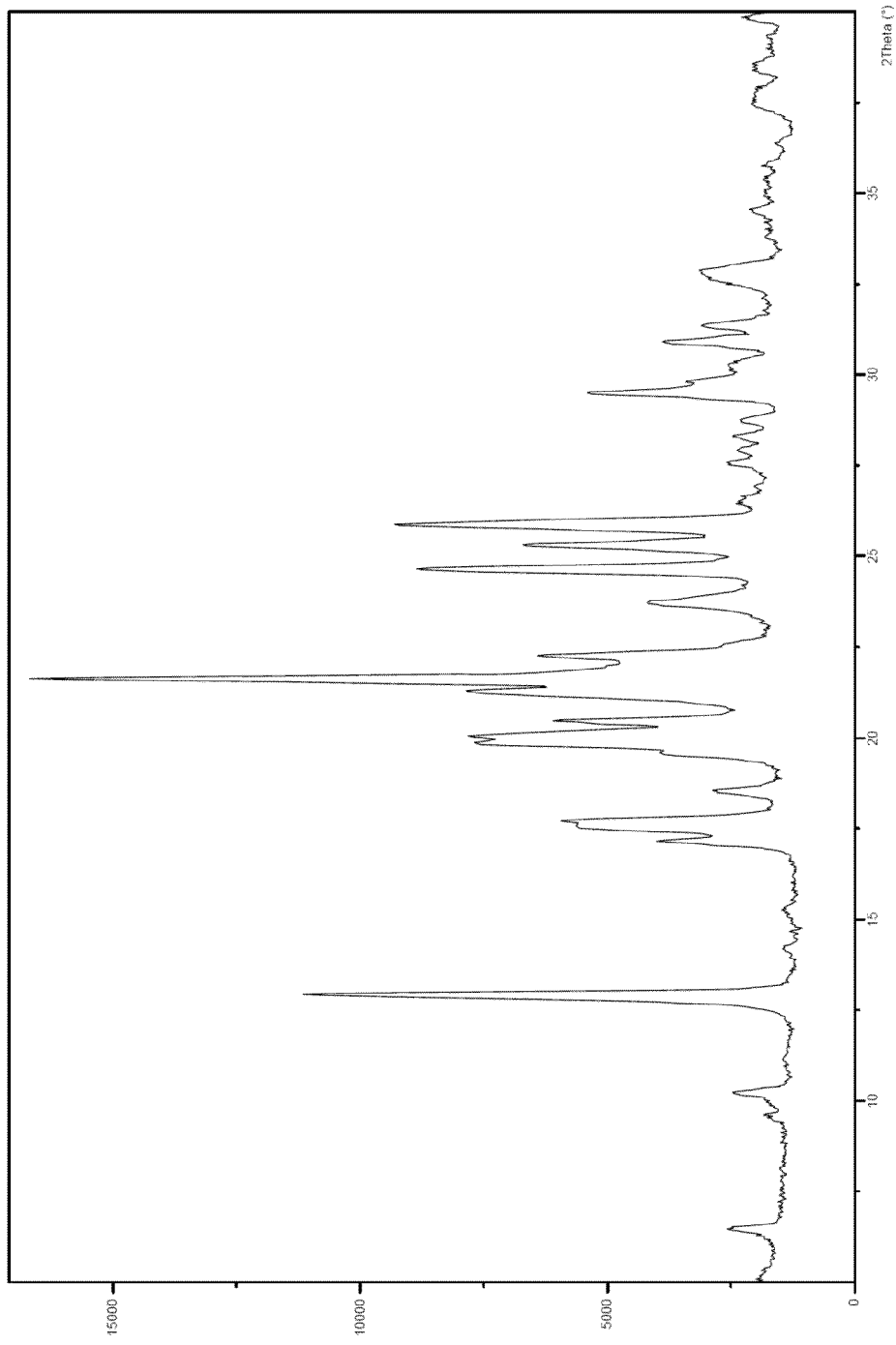
FIG. 6: PXRD of Compound 1 Hydrochloride Salt Form II.
Figure 7:
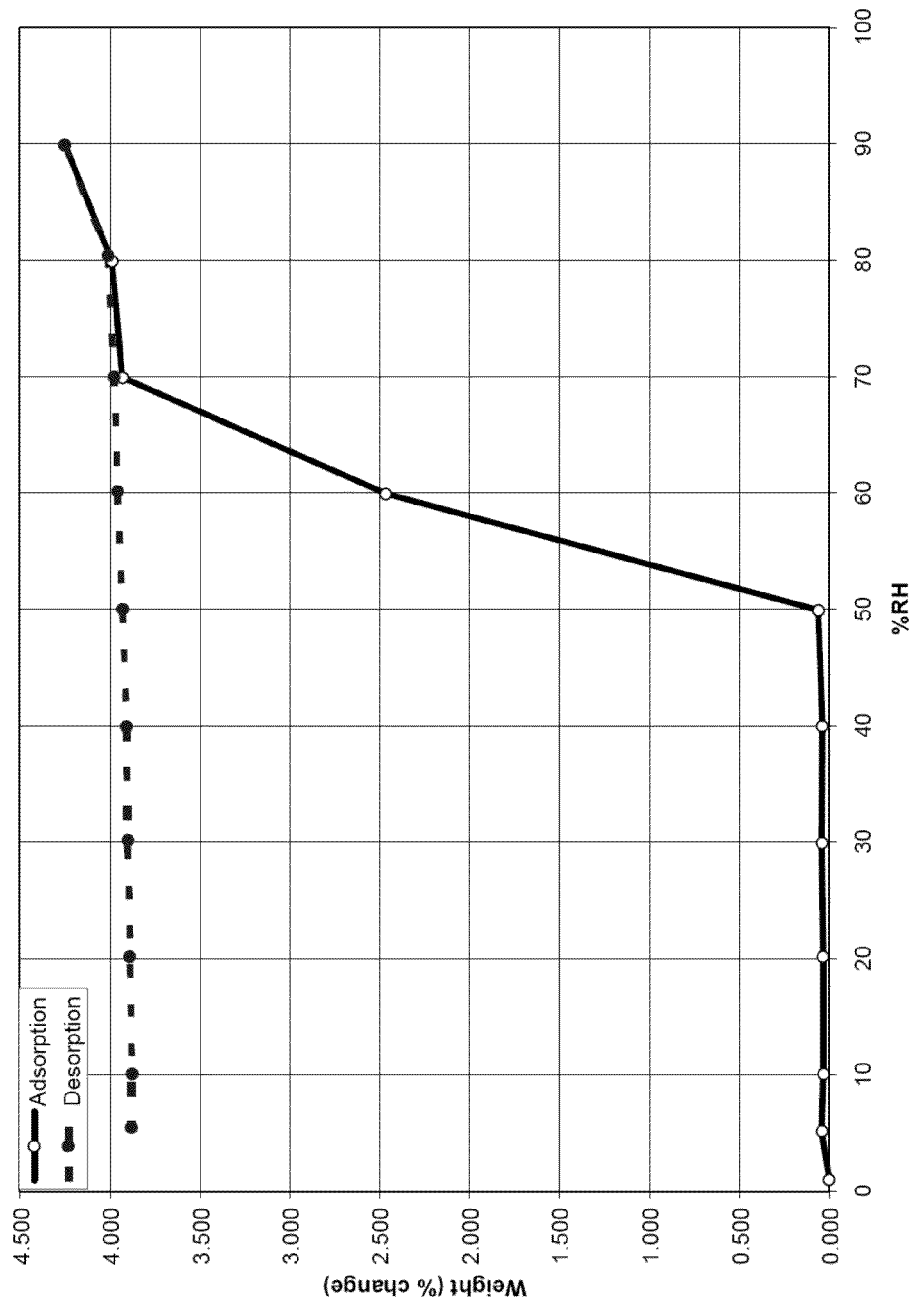
FIG. 7: DMS of Compound 1 Hydrochloride Salt Form II.

DSC analysis of the title salt is shown in FIG. 4. TGA analysis of the title salt is shown in FIG. 5. The powder X-ray diffraction pattern of the title salt is shown in FIG. 6. DMS analysis of the title salt is shown in FIG. 7.

Example 3

Preparation of (R)-8-Chloro-1-methyl-2,3,4,5-tetrahydro-1H-3-benzazepine Hydrochloride Hemihydrate Form III (Compound 1 Hydrochloride Salt Hemihydrate Form III)

Method 1

The title compound was prepared according to the methods described in U.S. Provisional Patent Application 61/268,930, which is incorporated herein by reference in its entirety.

Method 2

The title compound is prepared by solution-mediated phase transformation of Compound 1 hydrochloride salt Form IV in a medium with a water activity of ≥0.20.

Method 3

The title compound was prepared by exposing Compound 1 hydrochloride salt Form IV to relative humidity of 50% RH to 60% RH (during DMS).

The powder X-ray diffraction pattern of the title salt is shown in FIG. 8. DSC analysis of the title salt is shown in FIG.

Figure 10:
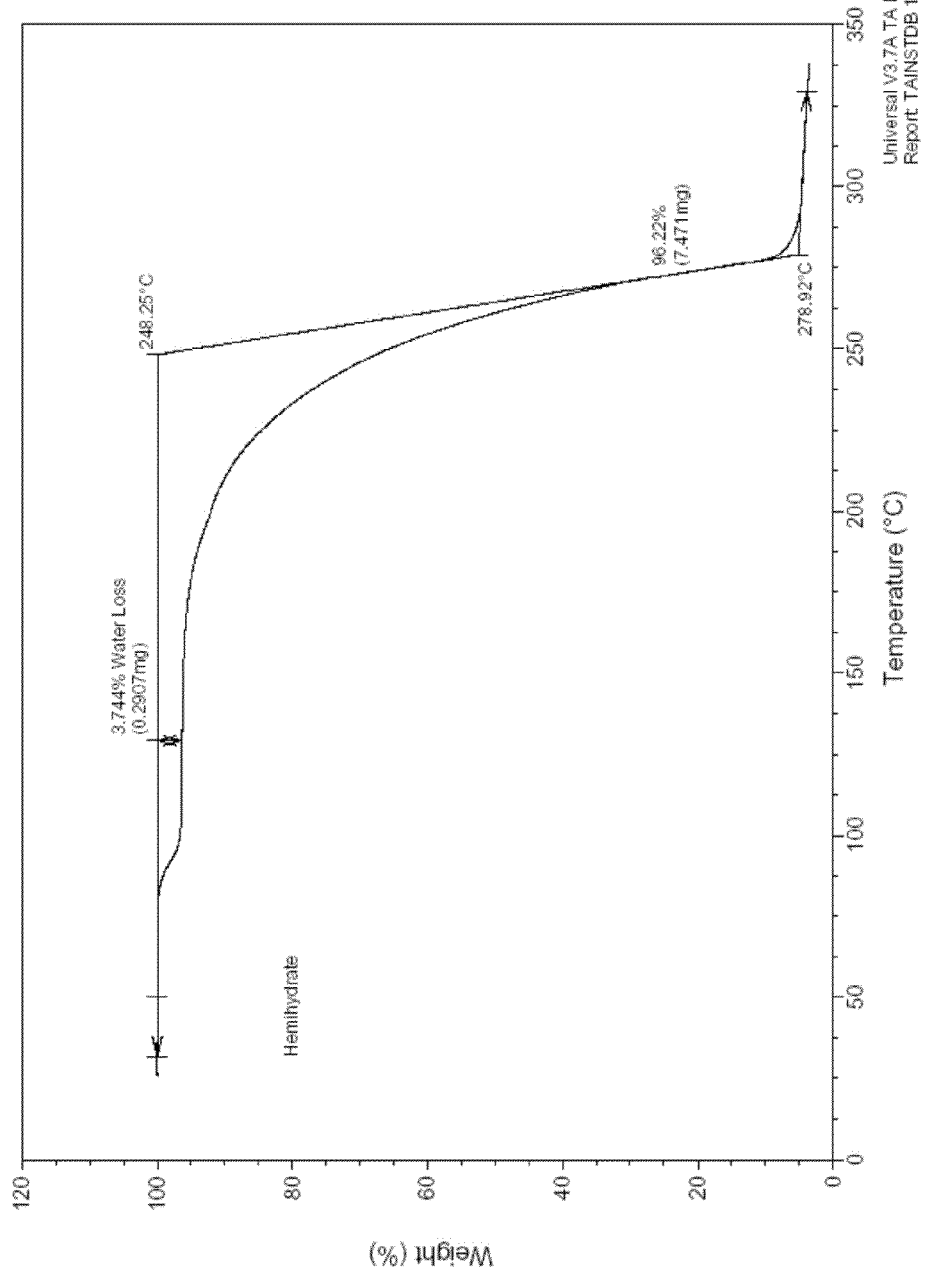
FIG. 10: TGA of Compound 1 Hydrochloride Salt Hemihydrate Form III.
Figure 11:
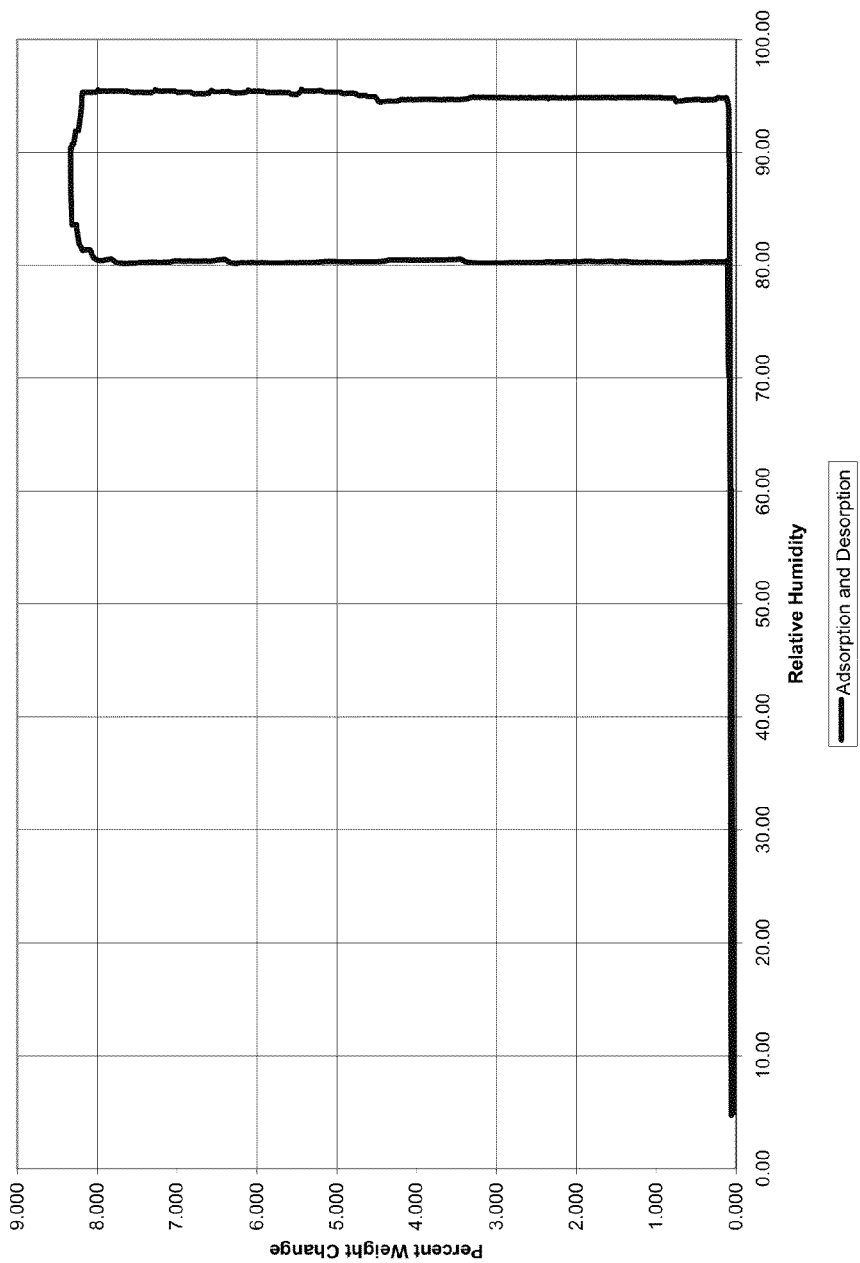
FIG. 11: DMS of Compound 1 Hydrochloride Salt Hemihydrate Form III.

9. TGA analysis of the title salt is shown in FIG. 10. DMS analysis of the title salt is shown in FIG. 11.

Example 4

Preparation of (R)-8-Chloro-1-methyl-2,3,4,5-tetrahydro-1H-3-benzazepine Hydrochloride Salt Form IV (Compound 1 Hydrochloride Salt Form IV)

Method 1

The title salt was obtained by slurrying Compound 1 hydrochloride salt Form II under anhydrous conditions in isobutanol, isopropanol, or acetonitrile at room temperature for two weeks.

Method 2

The title salt was obtained by slurrying Compound 1 hydrochloride salt Form I under anhydrous conditions in acetonitrile at room temperature for two days.

Method 3

The title salt was obtained by slurrying a mixture of Compound 1 hydrochloride salt hemihydrate Form III and acetonitrile, with a water activity of 0.04 at room temperature for two weeks.

Method 4

A mixture of Compound 1 hydrochloride salt Form IV (13 mg), Compound 1 hydrochloride salt Form I (525 mg) and acetonitrile (2 mL) was stirred over weekend at 18-25° C. The title compound (~300 mg) was isolated.

Method 5

Compound 1 hydrochloride salt hemihydrate Form III was dried in vacuum oven at 100° C. for 3 days to give Compound 1 hydrochloride salt Form II.

Compound 1 hydrochloride salt Form II (28 g) and Compound 1 hydrochloride salt

Form IV (25 mg) were stirred in acetonitrile (75 mL) at ~25° C. for 24 h. Conversion to the title salt was confirmed by PXRD, DSC, and TGA.

Figure 15:
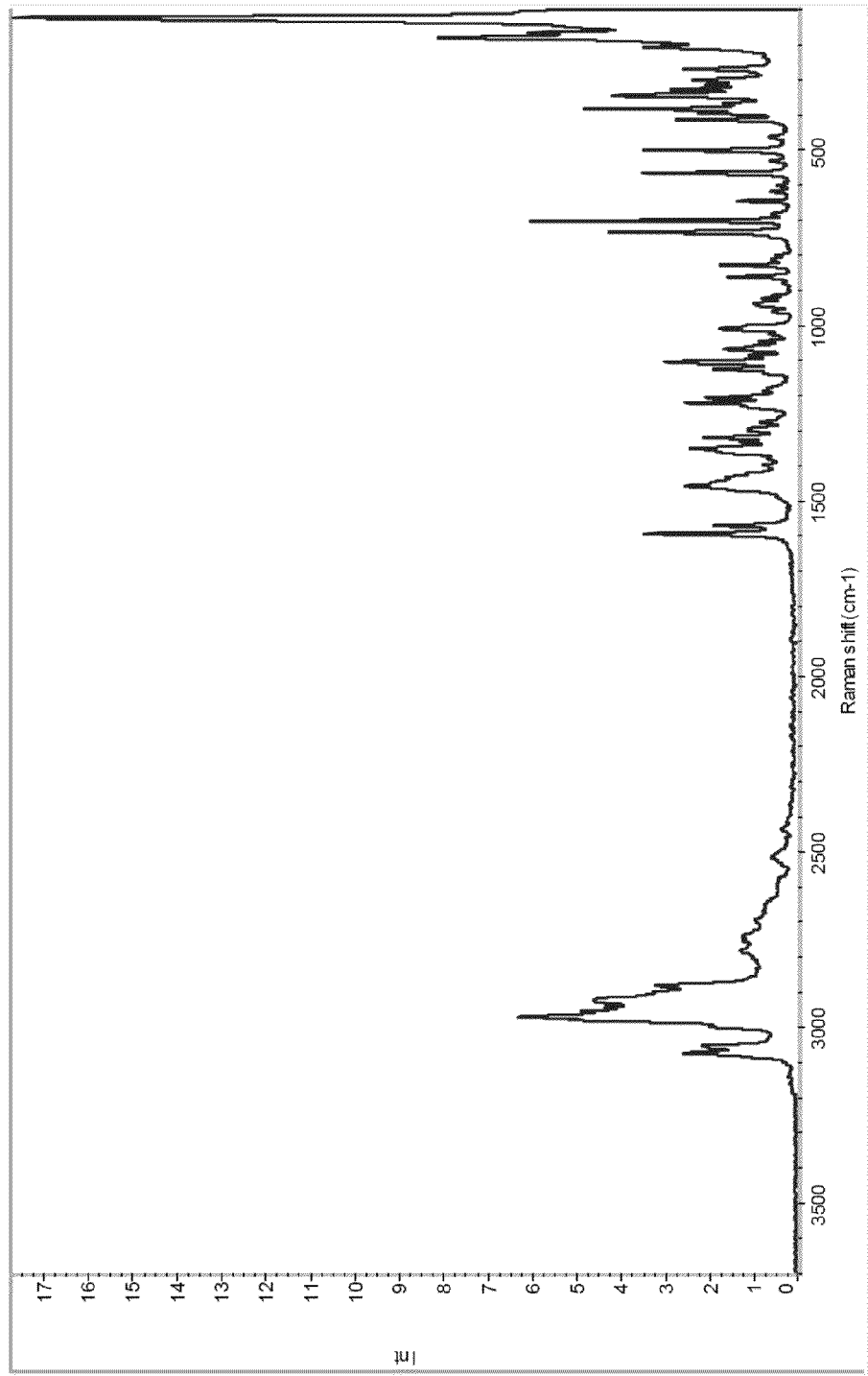
FIG. 15: Raman Spectrum of Compound 1 Hydrochloride Salt Form IV.

The powder X-ray diffraction pattern of the title salt is shown in FIG. 12. Thermal analysis (TGA and DSC) of the title salt are shown in FIG. 13. DMS analysis of the title salt is shown in FIG. 14. The Raman spectrum of the title salt is shown in FIG. 15.

Example 5

Critical Water Activity

The thermodynamic relationships between the Compound 1 hydrochloride salt hemihydrate Form III and the anhydrous polymorphs of Compound 1 hydrochloride salt were established by competitive slurry experiments in acetonitrile and acetone at various $a_w$, values.

Figure 16:
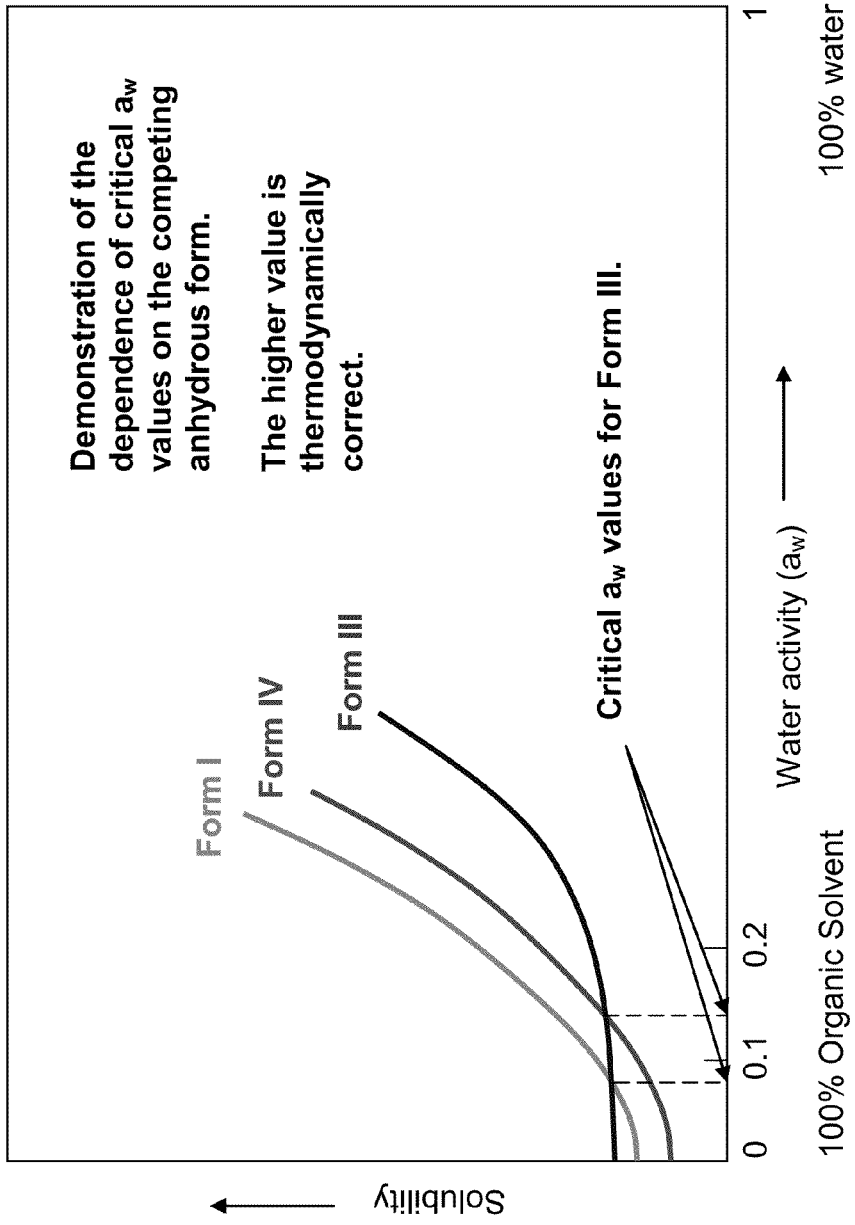
FIG. 16: Qualitative Relative Solubility of Compound 1 Hydrochloride Salt Form IV, Compound 1 Hydrochloride Salt Form I, and Compound 1 Hydrochloride Salt Hemihydrate Form III, as a Function of Water Activity.

At the critical $a_w$, a given anhydrous form and Compound 1 hydrochloride salt hemihydrate Form III will have equal solubility and can coexist in equilibrium. Below the critical $a_w$, the anhydrous form is more thermodynamically stable, thus less soluble. Above the critical water activity, Compound 1 hydrochloride salt hemihydrate Form III is more thermodynamically stable, thus less soluble. Solids from the competitive slurry experiments were identified by PXRD. Slurries with known $a_w$ values were used instead of humidity chambers because solution-mediated phase transformations (SMPTs) are much faster than vapor-mediated phase transformations, especially near the critical $a_w$. Only Compound 1 hydrochloride salt Form I and Compound 1 hydrochloride salt Form IV provided useful results since the studies were conducted at ambient temperature, where Compound 1 hydrochloride salt Form II is the least stable anhydrous polymorph and was very susceptible to conversion to Compound 1 hydrochloride salt Form I at very low $a_w$ values. FIG. 16 illustrates the critical $a_w$ of form Compound 1 hydrochloride salt hemihydrate Form III, with respect to Compound 1 hydrochloride salt Form I, and Compound 1 hydrochloride salt, IV.

Example 6

Enantiotropic Transition Temperature

Figure 17:
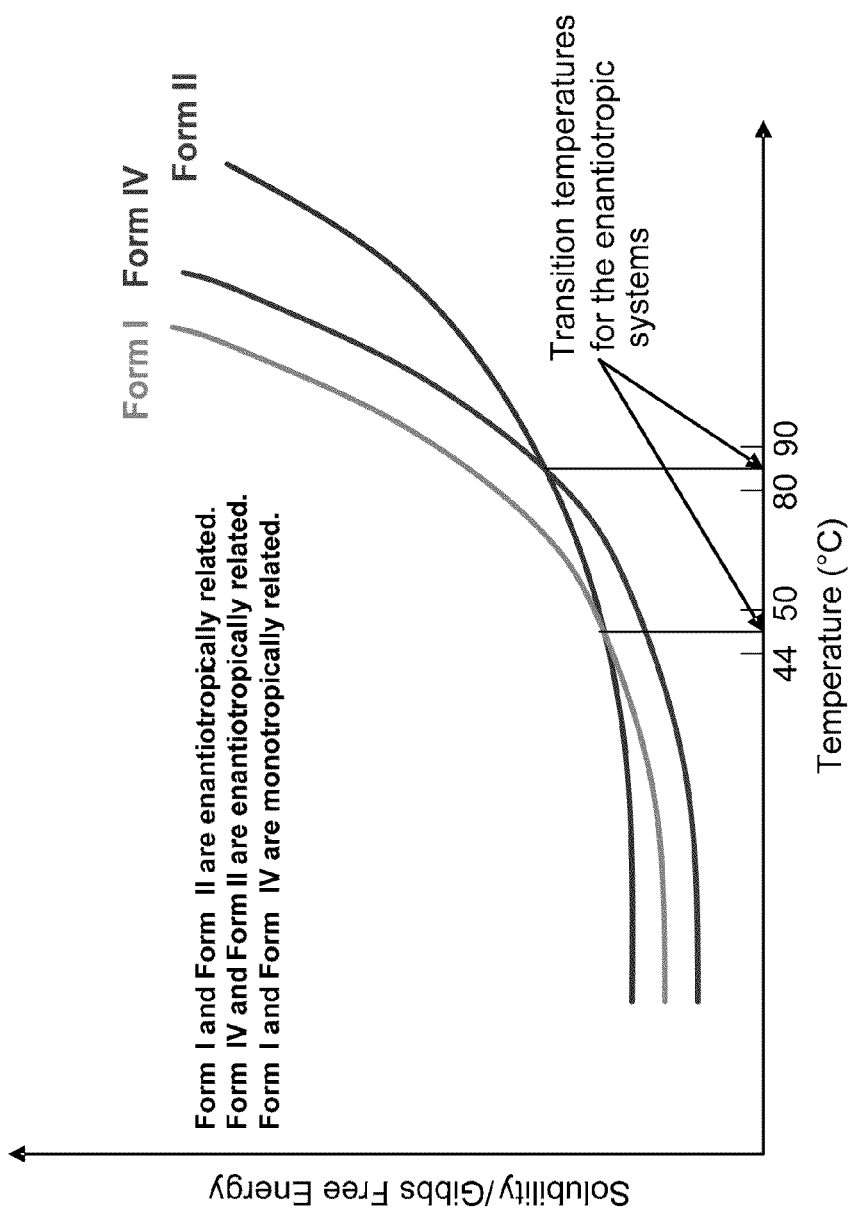
FIG. 17: Qualitative Relative Solubility/Gibbs Free Energy of Compound 1 Hydrochloride Salt Form I, Compound 1 Hydrochloride Salt Form II, and Compound 1 Hydrochloride Salt Form IV as a Function of Temperature.

For enantiotropic polymorphs, the temperature that marks the point at which two polymorphs have the same thermodynamic stability is called the transition temperature ($T_t$). The thermodynamic relationships between the anhydrous polymorphs of Compound 1 hydrochloride salt were established by competitive slurry experiments at various temperatures to allow SMPT to the more stable polymorph. Compound 1 hydrochloride salt Form I and Compound 1 hydrochloride salt, IV were shown to be enantiotropically related to Compound 1 hydrochloride salt Form II. Compound 1 hydrochloride salt Form I and Compound 1 hydrochloride salt, IV were shown to be monotropically related to each other (see FIG. 17).

Those skilled in the art will recognize that various modifications, additions, substitutions, and variations to the illustrative examples set forth herein can be made without departing from the spirit of the invention and are, therefore, considered within the scope of the invention.

What is claimed is:

1. A process for preparing (R)-8-chloro-1-methyl-2,3,4,5-tetrahydro-1H-3-benzazepine hydrochloride salt hemihydrate Form III, comprising slurrying a first mixture comprising: (R)-8-chloro-1-methyl-2,3,4,5-tetrahydro-1H-3-benzazepine hydrochloride salt Form IV; where said (R)-8-chloro-1-methyl-2,3,4,5-tetrahydro-1H-3-benzazepine hydrochloride salt Form IV has an X-ray power diffraction pattern comprising peaks, in terms of 2θ, at about 20.2316°, about 15.340017° and about 17.7719°; and a first solvent; to form said (R)-8-chloro-1-methyl-2,3,4,5-tetrahydro-1H-3-benzazepine hydrochloride salt Form III.

2. The process according to claim 1, wherein said first mixture has a water activity of greater than about 0.15.

3. The process according to claim 1, wherein said first mixture has a water activity of greater than about 0.20.

4. The process according to claim 1, wherein said (R)-8-chloro-1-methyl-2,3,4,5-tetrahydro-1H-3-benzazepine hydrochloride salt Form IV is prepared by slurrying a second mixture comprising: a starting material selected from (R)-8-chloro-1-methyl-2,3,4,5-tetrahydro-1H-3-benzazepine hydrochloride salt Form I, (R)-8-chloro-1-methyl-2,3,4,5-tetrahydro-1H-3-benzazepine hydrochloride salt Form II, and mixtures thereof; and a second solvent; to form said (R)-8-chloro-1-methyl-2,3,4,5-tetrahydro-1H-3-benzazepine hydrochloride salt Form IV.

5. The process according to claim 4, further comprising isolating said (R)-8-chloro-1-methyl-2,3,4,5-tetrahydro-1H-3-benzazepine hydrochloride salt Form IV.

6. The process according to claim 4, wherein said second mixture further comprises seed crystals, wherein said seed crystals comprise (R)-8-chloro-1-methyl-2,3,4,5-tetrahydro-1H-3-benzazepine hydrochloride salt Form IV.

7. The process according to claim 4, wherein said starting material comprises (R)-8-chloro-1-methyl-2,3,4,5-tetrahydro-1H-3-benzazepine hydrochloride salt Form I.

8. The process according to claim 4, wherein said starting material comprises (R)-8-chloro-1-methyl-2,3,4,5-tetrahydro-1H-3-benzazepine hydrochloride salt Form II.

9. The process according to claim 4, wherein said second mixture has a water activity of less than about 0.20.

10. The process according to claim 4, wherein said second mixture has a water activity of less than about 0.10.

11. The process according to claim 4, wherein said second mixture has a water activity of less than about 0.05.

12. The process according to claim 4, wherein said second solvent comprises an anhydrous solvent selected from: acetonitrile, isobutanol, acetone, and isopropanol.

13. The process according to claim 4, wherein said second solvent comprises acetonitrile.

14. A process according to claim 1, further comprising admixing said (R)-8-chloro-1-methyl-2,3,4,5-tetrahydro-1H-3-benzazepine hydrochloride salt hemihydrate Form III with a pharmaceutically acceptable carrier to produce a solid composition comprising (R)-8-chloro-1-methyl-2,3,4,5-tetrahydro-1H-3-benzazepine hydrochloride salt Form III.

15. A process according to claim 1, further comprising formulating said (R)-8-chloro-1-methyl-2,3,4,5-tetrahydro-1H-3-benzazepine hydrochloride salt hemihydrate Form III into a solid pharmaceutical composition.

16. A salt which is (R)-8-chloro-1-methyl-2,3,4,5-tetrahydro-1H-3-benzazepine hydrochloride salt Form IV, wherein said salt has an X-ray powder diffraction pattern comprising peaks, in terms of 2θ, at about 20.2316°, about 15.3400° and about 17.7719°.

17. The salt according to claim 16, having an X-ray powder diffraction pattern comprising peaks, in terms of 2θ, at about 20.2316°, about 15.3400°, about 17.7719°, about 25.1334°, about 23.2759°, about 18.2736°, about 35.8226°, about 19.8388°, about 10.6724°, and about 24.2509°.

18. A solid composition comprising a salt according to claim 16.

19. A solid pharmaceutical composition comprising a salt according to claim 16.

20. A method for weight management, comprising administering to an individual in need thereof, a therapeutically effective amount of a salt according to claim 16.

21. The method according to claim 20, wherein said weight management comprises weight loss.

22. The method according to claim 20, wherein said weight management comprises maintenance of weight loss.

23. The method according to claim 20, wherein said weight management further comprises a reduced-calorie diet.

24. The method according to claim 20, wherein said weight management further comprises a program of regular exercise.

25. The method according to claim 20, wherein said weight management further comprises both a reduced-calorie diet and a program of regular exercise.

26. The method according to claim 20, wherein said individual in need of weight management is an obese patient with an initial body mass index ≥30 kg/m$^2$.

27. The method according to claim 20, wherein said individual in need of weight management is an overweight patient with an initial body mass index ≥27 kg/m$^2$ in the presence of at least one weight related comorbid condition selected from: hypertension, dyslipidemia, cardiovascular disease, glucose intolerance, and sleep apnea.

28. The method according to claim 20, further comprising administering phentermine to said individual.

* * * * *